US012642676B2

(12) United States Patent
Tassoni et al.

(10) Patent No.: US 12,642,676 B2
(45) Date of Patent: Jun. 2, 2026

(54) MEDICAL IMPLANT ATTACHMENT MECHANISM

(71) Applicant: BOSTON SCIENTIFIC SCIMED, INC., Maple Grove, MN (US)

(72) Inventors: Nicholas Lee Tassoni, Andover, MN (US); Kelsey Rae Cooper, Blaine, MN (US); Thomas P. Jancaric, Maple Grove, MN (US); John D. Kroeger, Mounds View, MN (US); Eric Dinges, Edina, MN (US); Reggie Roth, Monticello, MN (US); John L. Teschendorf, Lino Lakes, MN (US); David B. Morris, Anoka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 159 days.

(21) Appl. No.: 17/716,592

(22) Filed: Apr. 8, 2022

(65) Prior Publication Data

US 2022/0273475 A1 Sep. 1, 2022

Related U.S. Application Data

(63) Continuation of application No. 16/280,582, filed on Feb. 20, 2019, now abandoned.

(Continued)

(51) Int. Cl.
*A61B 17/00* (2006.01)
*A61F 2/95* (2013.01)
*A61B 17/12* (2006.01)

(52) U.S. Cl.
CPC ...... *A61F 2/95* (2013.01); *A61B 2017/00867* (2013.01); *A61B 2017/12054* (2013.01); *A61F 2220/0025* (2013.01)

(58) Field of Classification Search
CPC .............................................. A61F 2220/0025
See application file for complete search history.

(56) References Cited

U.S. PATENT DOCUMENTS 5,117,839 A 6/1992 Dance
5,234,437 A 8/1993 Sepetka
(Continued)

FOREIGN PATENT DOCUMENTS

EP 1792575 A1 6/2007
EP 1792576 A1 6/2007
(Continued)

OTHER PUBLICATIONS

International Search Report and Written Opinion for International Application No. PCT/US2017/061779 mailed Feb. 28, 2018.

(Continued)

*Primary Examiner* — Jacqueline Woznicki
(74) *Attorney, Agent, or Firm* — Seager, Tufte & Wickhem LLP

(57) ABSTRACT

An attachment mechanism for a medical implant system may include a first part fixedly attached to a distal end of an elongate shaft, the first part having a first longitudinal lumen configured to slidably receive a release wire disposed within the elongate shaft, and a second part fixedly attached to a proximal end of a medical implant, the second part having a second longitudinal lumen configured to slidably receive the release wire. A tubular distal portion of the second part may include an engagement feature configured to non-releasably engage the second part with the medical implant.

13 Claims, 16 Drawing Sheets

Related U.S. Application Data

(60) Provisional application No. 62/634,498, filed on Feb. 23, 2018.

(56) References Cited

U.S. PATENT DOCUMENTS

| | | | |
|---|---|---|---|
| 5,250,071 A | 10/1993 | Palermo | |
| 5,282,478 A | 2/1994 | Fleischhaker, Jr. et al. | |
| 5,304,195 A | 4/1994 | Twyford, Jr. et al. | |
| 5,312,415 A | 5/1994 | Palmero | |
| 5,546,958 A | 8/1996 | Thorud et al. | |
| RE37,117 E | 3/2001 | Palmero | |
| 6,277,125 B1 | 8/2001 | Barry et al. | |
| 6,491,646 B1 | 12/2002 | Blackledge | |
| 7,044,134 B2 | 5/2006 | Khairkhahan et al. | |
| 7,708,755 B2 | 5/2010 | Davis et al. | |
| 7,815,661 B2 | 10/2010 | Mirizzi et al. | |
| 7,896,899 B2 | 3/2011 | Patterson et al. | |
| 8,142,456 B2 | 3/2012 | Rosqueta et al. | |
| 8,236,042 B2 | 8/2012 | Berez et al. | |
| 8,317,821 B1 | 11/2012 | Ashby et al. | |
| 8,333,786 B2 | 12/2012 | Mirizzi et al. | |
| 8,333,796 B2 | 12/2012 | Tompkins et al. | |
| 8,641,777 B2 | 2/2014 | Strauss et al. | |
| 8,696,701 B2 | 4/2014 | Becking et al. | |
| 8,747,597 B2 | 6/2014 | Rosqueta et al. | |
| 8,795,313 B2 | 8/2014 | Liang et al. | |
| 8,801,746 B1 | 8/2014 | Kreidler et al. | |
| 8,911,487 B2 | 12/2014 | Bennett et al. | |
| 9,017,350 B2 | 4/2015 | Karabey et al. | |
| 9,017,361 B2 | 4/2015 | Karabey et al. | |
| 9,060,773 B2 | 6/2015 | Nguyen et al. | |
| 9,119,948 B2 | 9/2015 | Lee et al. | |
| 9,186,151 B2 | 11/2015 | Tompkins et al. | |
| 9,198,670 B2 | 12/2015 | Hewitt et al. | |
| 9,301,827 B2 | 4/2016 | Strauss et al. | |
| 9,307,999 B2 | 4/2016 | Li et al. | |
| 9,468,442 B2 | 10/2016 | Huynh et al. | |
| 9,498,226 B2 | 11/2016 | Cage et al. | |
| 9,549,740 B2 | 1/2017 | Rees | |
| 9,554,805 B2 | 1/2017 | Tompkins et al. | |
| 2005/0137709 A1* | 6/2005 | Klotz | A61F 2/4261 |
| | | | 623/21.12 |
| 2006/0022462 A1 | 2/2006 | Hull et al. | |
| 2006/0036281 A1 | 2/2006 | Patterson et al. | |
| 2006/0212055 A1 | 9/2006 | Karabey et al. | |
| 2006/0229669 A1 | 10/2006 | Mirizzi et al. | |
| 2006/0282159 A1 | 12/2006 | Taheri | |
| 2007/0135826 A1 | 6/2007 | Zaver et al. | |
| 2007/0270903 A1 | 11/2007 | Davis et al. | |
| 2007/0282373 A1 | 12/2007 | Ashby et al. | |
| 2007/0293928 A1 | 12/2007 | Tomlin | |
| 2008/0109059 A1 | 5/2008 | Gordon et al. | |
| 2008/0119891 A1 | 5/2008 | Miles et al. | |
| 2008/0300616 A1 | 12/2008 | Que et al. | |
| 2009/0043331 A1 | 2/2009 | Buiser et al. | |
| 2009/0062838 A1 | 3/2009 | Brumleve et al. | |
| 2009/0062845 A1 | 3/2009 | Tekulve | |
| 2009/0163934 A1 | 6/2009 | Raschdorf, Jr. et al. | |
| 2009/0177261 A1 | 7/2009 | Teoh et al. | |
| 2009/0270978 A1 | 10/2009 | Virkler et al. | |
| 2009/0287291 A1 | 11/2009 | Becking et al. | |
| 2009/0287294 A1 | 11/2009 | Rosqueta et al. | |
| 2010/0106178 A1 | 4/2010 | Obermiller et al. | |
| 2010/0121350 A1 | 5/2010 | Mirigian | |
| 2010/0174269 A1 | 7/2010 | Tompkins et al. | |
| 2011/0166588 A1 | 7/2011 | Connor et al. | |
| 2011/0184454 A1 | 7/2011 | Barry et al. | |
| 2011/0202085 A1 | 8/2011 | Loganathan et al. | |
| 2011/0238147 A1 | 9/2011 | Bennett et al. | |
| 2011/0265943 A1 | 11/2011 | Rosqueta et al. | |
| 2011/0319926 A1 | 12/2011 | Becking et al. | |
| 2012/0046687 A1 | 2/2012 | Trommeter et al. | |
| 2012/0083874 A1* | 4/2012 | Dale | A61F 2/2427 |
| | | | 623/2.11 |
| 2012/0203322 A1 | 8/2012 | Eells | |
| 2012/0283812 A1 | 11/2012 | Lagodzki et al. | |
| 2012/0316598 A1 | 12/2012 | Becking et al. | |
| 2012/0330341 A1 | 12/2012 | Becking et al. | |
| 2012/0330347 A1 | 12/2012 | Becking et al. | |
| 2012/0330348 A1 | 12/2012 | Strauss et al. | |
| 2013/0066360 A1 | 3/2013 | Becking et al. | |
| 2013/0072961 A1 | 3/2013 | Cage et al. | |
| 2013/0085520 A1 | 4/2013 | Liang et al. | |
| 2013/0085522 A1 | 4/2013 | Becking et al. | |
| 2013/0152941 A1 | 6/2013 | Nguyen et al. | |
| 2013/0253572 A1 | 9/2013 | Molaei et al. | |
| 2013/0261730 A1 | 10/2013 | Bose et al. | |
| 2013/0296917 A1 | 11/2013 | Rees | |
| 2013/0331882 A1 | 12/2013 | Tompkins et al. | |
| 2014/0058434 A1 | 2/2014 | Jones et al. | |
| 2014/0058435 A1 | 2/2014 | Jones et al. | |
| 2014/0128907 A1 | 5/2014 | Hui et al. | |
| 2014/0135810 A1 | 5/2014 | Divino et al. | |
| 2014/0135811 A1 | 5/2014 | Divino et al. | |
| 2014/0135812 A1 | 5/2014 | Divino et al. | |
| 2014/0148843 A1 | 5/2014 | Strauss et al. | |
| 2014/0172001 A1 | 6/2014 | Becking et al. | |
| 2014/0236127 A1 | 8/2014 | Lee et al. | |
| 2014/0358175 A1 | 12/2014 | Tompkins et al. | |
| 2015/0005807 A1 | 1/2015 | Lagodzki et al. | |
| 2015/0073524 A1 | 3/2015 | Bennett et al. | |
| 2015/0112378 A1 | 4/2015 | Torp | |
| 2015/0157332 A1 | 6/2015 | Obermiller et al. | |
| 2015/0196304 A1 | 7/2015 | Rabkin et al. | |
| 2015/0230802 A1 | 8/2015 | Lagodzki et al. | |
| 2015/0257763 A1 | 9/2015 | Blum et al. | |
| 2015/0272589 A1 | 10/2015 | Lorenzo | |
| 2015/0297240 A1 | 10/2015 | Divino et al. | |
| 2015/0327868 A1 | 11/2015 | Islak et al. | |
| 2015/0335333 A1 | 11/2015 | Jones et al. | |
| 2015/0342611 A1 | 12/2015 | Leopold et al. | |
| 2015/0343181 A1 | 12/2015 | Bradway et al. | |
| 2016/0008003 A1 | 1/2016 | Kleshinski et al. | |
| 2016/0022445 A1 | 1/2016 | Ruvalcaba et al. | |
| 2016/0030052 A1 | 2/2016 | Cragg et al. | |
| 2016/0166257 A1 | 6/2016 | Allen et al. | |
| 2016/0192942 A1 | 7/2016 | Strauss et al. | |
| 2016/0228123 A1 | 8/2016 | Anderson et al. | |
| 2016/0228124 A1 | 8/2016 | Trommeter et al. | |
| 2016/0228128 A1 | 8/2016 | Connolly | |
| 2016/0317274 A1 | 11/2016 | Liu et al. | |
| 2021/0402159 A1* | 12/2021 | Harder | A61B 17/12136 |

FOREIGN PATENT DOCUMENTS

| | | | |
|---|---|---|---|
| EP | 2777542 A2 | 9/2014 | |
| EP | 2777545 A2 | 9/2014 | |
| EP | 3085310 A1 | 10/2016 | |
| JP | 2016537134 A | 12/2016 | |
| WO | 9406503 A1 | 3/1994 | |
| WO | 0232496 A1 | 4/2002 | |
| WO | 2007047111 A1 | 4/2007 | |
| WO | 2007070797 A2 | 6/2007 | |
| WO | 2010030993 A1 | 3/2010 | |
| WO | 2010098804 A1 | 9/2010 | |
| WO | 2013112944 A1 | 8/2013 | |
| WO | 2014145012 A2 | 9/2014 | |
| WO | 2014145005 A3 | 4/2015 | |

OTHER PUBLICATIONS

International Search Report and Written Opinion for International Application No. PCT/US2018/028240 mailed Jul. 13, 2018.
International Search Report and Written Opinion for International Application No. for PCT/US2018/000148 mailed Dec. 5, 2018.
International Search Report & Written Opinion for International Application No. for PCT/US2018/021978 mailed Jun. 15, 2018.
International Search Report and Written Opinion for International Application No. PCT/US2019/18724 mailed May 31, 2019.

* cited by examiner

MEDICAL IMPLANT ATTACHMENT MECHANISM

CROSS-REFERENCE TO RELATED APPLICATIONS

This application is a continuation of U.S. application Ser. No. 16/280,582, filed Feb. 20, 2019, which claims the benefit of priority under 35 U.S.C. § 119 to U.S. Provisional Application Ser. No. 62/634,498, filed Feb. 23, 2018, the entirety of which is incorporated herein by reference.

TECHNICAL FIELD

The present disclosure pertains to medical devices and methods for manufacturing and/or using medical devices. More particularly, the present disclosure pertains to configurations of an attachment mechanism in a system for releasing medical implants.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, occlusive devices, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, an attachment mechanism for a medical implant system may comprise a first part fixedly attached to a distal end of an elongate shaft; and a second part fixedly attached to a proximal end of a medical implant. A tubular distal portion of the second part may include an engagement feature configured to non-releasably engage the second part with the medical implant.

In addition or alternatively, and in a second aspect, the second part is formed from a first metallic material, and the medical implant is formed from a second metallic material dissimilar from the first metallic material.

In addition or alternatively, and in a third aspect, the second metallic material is a shape memory alloy.

In addition or alternatively, and in a fourth aspect, the engagement feature includes one or more recesses extending into an outer surface of the tubular distal portion of the second part.

In addition or alternatively, and in a fifth aspect, a portion of the medical implant extends into the one or more recesses.

In addition or alternatively, and in a sixth aspect, the portion of the medical implant extending into the one or more recesses includes a movable tab biased radially inward.

In addition or alternatively, and in a seventh aspect, the portion of the medical implant extending into the one or more recesses includes at least one plug inserted through a window in the medical implant.

In addition or alternatively, and in an eighth aspect, the at least one plug is fixedly attached to the medical implant after the at least one plug is inserted through the window.

In addition or alternatively, and in a ninth aspect, the engagement feature includes at least one protrusion extending radially outward from an outer surface of the tubular distal portion of the second part.

In addition or alternatively, and in a tenth aspect, the medical implant includes at least one window extending through a wall of the medical implant configured to receive the at least one protrusion.

In addition or alternatively, and in an eleventh aspect, the medical implant includes at least one longitudinally-oriented cut extending distally from the proximal end of the medical implant.

In addition or alternatively, and in a twelfth aspect, material on opposing sides of the at least one longitudinally-oriented cut is fixedly secured together after the tubular distal portion of the second part is inserted into the proximal end of the medical implant.

In addition or alternatively, and in a thirteenth aspect, an attachment mechanism for an medical implant system may comprise a first part fixedly attached to a distal end of an elongate shaft; and a second part fixedly attached to a proximal end of an medical implant. A tubular proximal portion of the first part may include an engagement feature configured to non-releasably engage the first part with the elongate shaft. A tubular distal portion of the second part may include an engagement feature configured to non-releasably engage the second part with the medical implant.

In addition or alternatively, and in a fourteenth aspect, the first part and the second part are configured to interlock with each other such that relative axial translation between the first part and the second part is prevented when the first part abuts the second part and a first longitudinal lumen of the first part is aligned coaxially with a second longitudinal lumen of the second part.

In addition or alternatively, and in a fifteenth aspect, the first part and the second part are configured to interlock with each other such that relative lateral translation between the first part and the second part is prevented when the first part abuts the second part, the first longitudinal lumen is aligned coaxially with the second longitudinal lumen, and the release wire is slidably engaged with the first longitudinal lumen and the second longitudinal lumen.

In addition or alternatively, and in a sixteenth aspect, a method of making a medical implant system may comprise:

inserting a first part of an attachment mechanism into a distal end of an elongate shaft and securing the first part to the elongate shaft;

inserting a second part of the attachment mechanism into a proximal end of a medical implant, wherein the second part is formed from a first metallic material and the medical implant is formed from a second metallic material dissimilar from the first metallic material; and applying heat to the medical implant to fixedly attach the second part to the medical implant.

In addition or alternatively, and in a seventeenth aspect, applying heat to the medical implant causes a portion of the medical implant to reflow into one or more recesses extending into an outer surface of the second part.

In addition or alternatively, and in an eighteenth aspect, applying heat to the medical implant includes welding the medical implant to itself.

In addition or alternatively, and in a nineteenth aspect, applying heat to the medical implant includes heating a plug inserted through a window in the medical implant such that the plug reflows with the medical implant and becomes integrated with the medical implant.

In addition or alternatively, and in a twentieth aspect, the first part is formed from the first metallic material and the elongate shaft is formed from a third metallic material dissimilar from the first metallic material. The method may further comprise applying heat to the distal end of the elongate shaft to fixedly attach the first part to the distal end of the elongate shaft.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
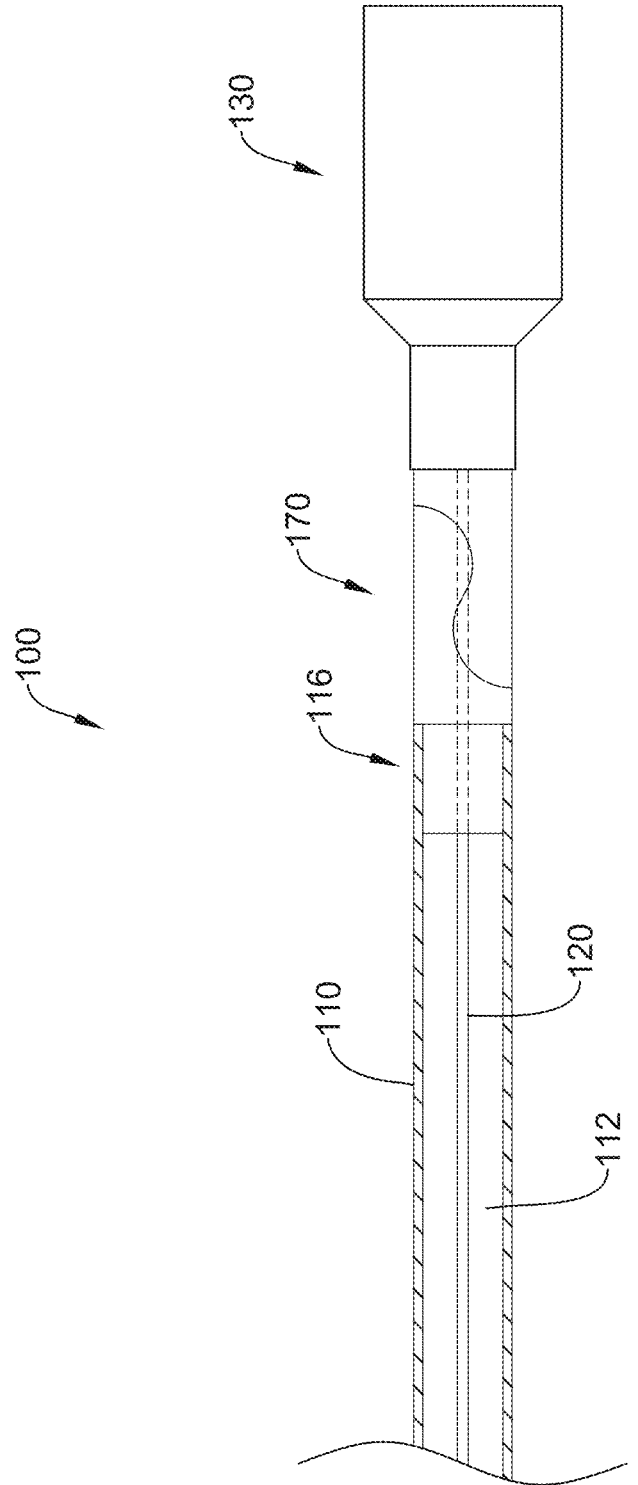
FIG. 1 is a partial cut-away view of an example medical implant system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless specifically referred to as a minimum extent. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. However, where referred to as a "minimum extent", the "extent" shall refer to a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

FIG. 1 illustrates aspects of an example medical implant system 100. The medical implant system 100 may include an elongate shaft 110 having a lumen 112 extending from a proximal end of the elongate shaft 110 to a distal end 116 of the elongate shaft 110. In some embodiments, the elongate shaft 110 may be a catheter, a hypotube, or other similar tubular structure. In some embodiments, at least a portion of the elongate shaft 110 may include micromachining, a plurality of cuts or weakened areas, some degree of material removal, etc. to provide increased flexibility along a length of the elongate shaft 110 while maintaining pushability for navigating tortuous vasculature. Some suitable but non-limiting materials for the elongate shaft 110, for example metallic materials, polymer materials, composite materials, etc., are described below.

The medical implant system 100 may include a release wire 120 slidably disposed within the lumen 112 of the elongate shaft 110. A medical implant 130 may be disposed proximate the distal end 116 of the elongate shaft 110. The release wire 120 may be axially slidable between an inter-locked position (e.g., FIG. 1) and a released position (e.g., FIG. 2, described further below). A distal portion of the release wire 120 may be configured to releasably attach the medical implant 130 to the distal end 116 of the elongate shaft 110. The medical implant 130 may be configured to expand and/or shift from a delivery configuration to a deployed configuration. For simplicity, the medical implant 130 is generically illustrated herein as an occlusive medical device, but other suitable medical devices transported, delivered, used, released, etc. in a similar manner are also contemplated, including but not limited to, embolic coils, stents, embolic filters, replacement heart valves, vascular occlusion devices, other occlusion devices, and/or other medical implants, etc. In some embodiments, the release wire 120 may be alternately and/or interchangeably referred to as a pull wire, an actuation wire, and/or a locking wire. The release wire 120 may generally be a solid wire or shaft, but may also be tubular in some embodiments. In some embodiments, the release wire 120 may be absent and/or unnecessary. Some suitable but non-limiting materials for the release wire 120 and/or the medical implant 130, for example metallic materials, polymer materials, composite materials, shape memory materials, etc., are described below.

In some embodiments, the medical implant system 100 may include a microcatheter sized and configured to deliver the medical implant 130 to a treatment site in a delivery configuration. The elongate shaft 110 and the medical implant 130 may be slidably disposed within a lumen of the microcatheter. In some embodiments, the microcatheter may facilitate percutaneous delivery of the medical implant 130 to the treatment site. In some embodiments, the medical implant 130 may be radially and/or longitudinally constrained into a delivery configuration when the medical implant 130 is disposed within the lumen of the microcatheter. Some suitable but non-limiting materials for the microcatheter, for example metallic materials, polymer materials, composite materials, etc., are described below.

In at least some embodiments, the medical implant system 100 may include a securement member fixedly attached to and/or extending proximally from the proximal end of the elongate shaft 110, and fixedly attached to a proximal end of the release wire 120. The securement member may include a proximal portion and a distal portion. In some embodiments, the proximal portion of the securement member may be fixedly attached to the distal portion of the securement member. In some embodiments, the proximal portion of the securement member may be integrally formed with the distal portion of the securement member as a single unitary structure. The proximal portion of the securement member may take one or more of several different forms, including but not limited to, a generally solid member, a tubular member, or combinations thereof. For example, the proximal portion of the securement member may include an axial lumen extending along a central longitudinal axis of the medical implant system 100, the elongate shaft 110, the release wire 120, and/or the securement member, the axial lumen being configured to receive a proximal end of the release wire 120.

In some embodiments, the proximal portion of the securement member may be configured to translate proximally away from the proximal end of the elongate shaft 110 upon application of a proximally-directed force to the proximal portion of the securement member while the elongate shaft 110 is maintained in a fixed position. The distal portion of the securement member may be fixedly attached to the proximal end of the elongate shaft 110. In at least some embodiments, an outer surface of the distal portion of the securement member may be fixedly attached to an inner surface of the elongate shaft 110 (e.g., a surface defining the lumen 112). In some embodiments, an inner surface of the distal portion of the securement member may be fixedly attached to an outer surface of the elongate shaft 110. In some embodiments, a distal end of the distal portion of the securement member may be embedded in the proximal end of the elongate shaft 110. In some embodiments, the distal portion may be integrally formed with and/or from the elongate shaft 110.

A wall of the distal portion of the securement member may define a lumen, wherein the release wire 120 is slidably disposed within the lumen of the distal portion of the securement member. The lumen of the distal portion of the securement member may be coaxial with and/or fluidly connected to the lumen 112 of the elongate shaft 110. Proximal axial translation of the proximal portion of the securement member away from and/or relative to the proximal end of the elongate shaft 110 may translate the release wire 120 relative to the elongate shaft 110 from the interlocked position to the released position to release the medical implant 130 from the distal end 116 of the elongate shaft 110, as described herein.

Figure 2:
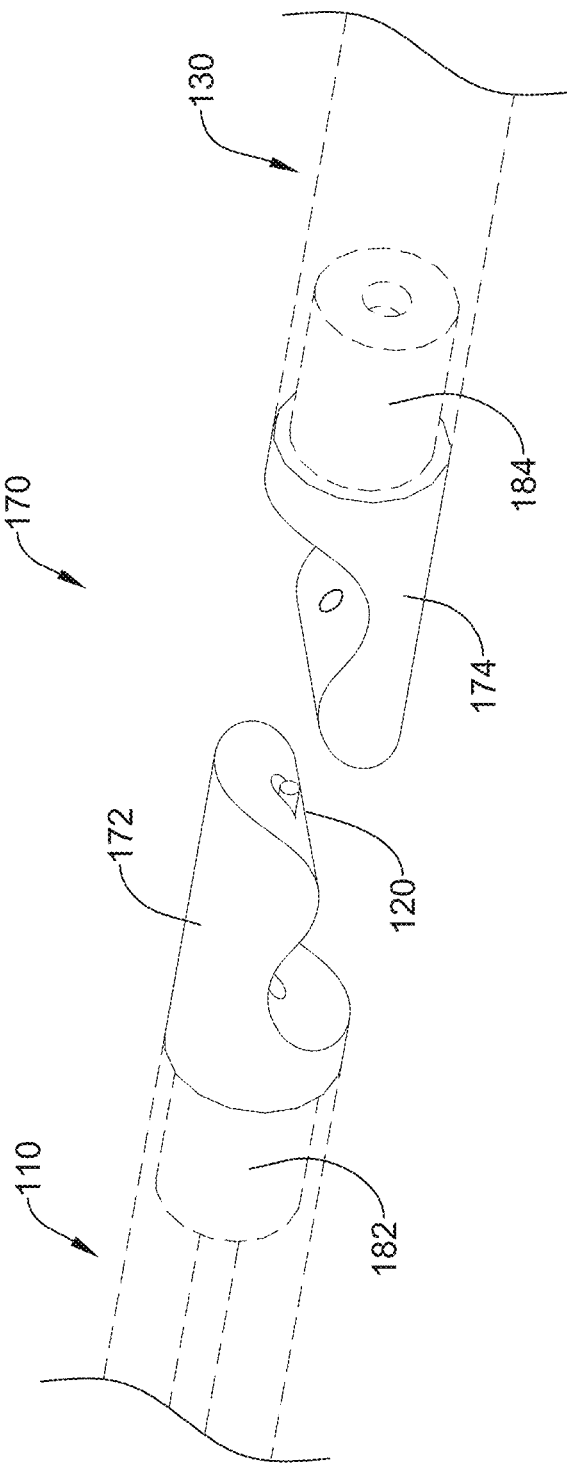
FIG. 2 illustrates an example attachment mechanism of an example medical implant system.

FIGS. 1 and 2 generally illustrate the medical implant 130 being released from the elongate shaft 110, such as at a treatment site, for example. In use, the microcatheter of the medical implant system 100 may be inserted into a patient's anatomy and a distal end of the microcatheter may be guided and/or advanced to a location adjacent a treatment site. The medical implant 130 disposed at and/or proximate the distal end 116 of the elongate shaft 110 may be inserted into a proximal end of the lumen disposed within the microcatheter and advanced through and/or with the microcatheter to the treatment site. In some embodiments, the medical implant 130 may be disposed within the lumen of the microcatheter proximate a distal end of the microcatheter. In some embodiments, the medical implant 130 may be disposed within the lumen of the microcatheter proximate the distal end of the microcatheter prior to use and/or prior to inserting the microcatheter into the patient's anatomy. Deployment and/or release of the medical implant 130 may be performed selectively depending upon the type of medical device and/or the desired treatment process or method. When ready to deploy the medical implant 130, the elongate shaft 110 may be advanced and/or translated distally relative to the microcatheter until the medical implant 130 is exposed and/or disposed distal of the microcatheter. Alternatively, the microcatheter may be withdrawn relative to the elongate shaft 110 until the medical implant 130 is exposed and/or disposed distal of the microcatheter.

In use, the elongate shaft 110 may have sufficient length that the proximal end of the elongate shaft 110 and/or the securement member remains proximal of (e.g., extends proximally from) the microcatheter when the medical implant 130 is disposed distal of the microcatheter. In use, the elongate shaft 110 may have sufficient length to reach from the treatment site to a position outside of the patient where the medical implant system 100 may be manipulated by an operator (e.g., clinician, physician, user, etc.). After insertion of the medical implant system 100 to the treatment site, the operator of the medical implant system 100 may place a first hand on the proximal end of the elongate shaft 110 and a second hand on the proximal portion of the securement member in order to manipulate the proximal portion of the securement member and/or the release wire 120 relative to the elongate shaft 110 to release the medical implant 130. In at least some embodiments, the distal portion of the securement member may be disposed proximal of a proximal end of the microcatheter when the medical implant 130 is disposed distal of the microcatheter.

An attachment mechanism 170 may releasably attach the medical implant 130 to the distal end 116 of the elongate shaft 110. The attachment mechanism 170 may cooperate with the release wire 120 to releasably attach the medical implant 130 to the distal end 116 of the elongate shaft 110. In some embodiments, the elongate shaft 110 may include a first part 172 of the attachment mechanism 170 fixedly and non-reversibly (e.g., permanently) attached to the distal end 116 of the elongate shaft 110 and the medical implant 130 may include a second part 174 of the attachment mechanism 170 fixedly and non-reversibly (e.g., permanently) attached to a proximal end of the medical implant 130. Some suitable but non-limiting materials for the attachment mechanism 170, the first part 172, and the second part 174, for example metallic materials, polymer materials, composite materials, shape memory materials, etc., are described below.

A distal portion and/or a distal end of the release wire 120 may slidably engage with the first part 172 of the attachment mechanism 170 and the second part 174 of the attachment mechanism 170 in the interlocked position, to interlock the first part 172 of the attachment mechanism 170 with the second part 174 of the attachment mechanism 170, as shown in FIG. 1. When the proximal portion of the securement member is translated proximally away from the proximal end of the elongate shaft 110, the release wire 120 may be translated in a proximal direction relative to the elongate shaft 110 toward the released position to release the second part 174 of the attachment mechanism 170 and/or the medical implant 130 from the first part 172 of the attachment mechanism 170 and/or the elongate shaft 110, as shown in FIG. 2. In at least some embodiments, the release wire 120 may be slidably disposed within the distal portion of the securement member, the lumen 112 extending through the elongate shaft 110, a first longitudinal lumen extending through the first part 172 of the attachment mechanism 170, and a second longitudinal lumen extending through the second part 174 of the attachment mechanism 170. The first longitudinal lumen of the first part 172 and the second longitudinal lumen of the second part 174 may be substantially coaxial with the central longitudinal axis and/or the release wire 120 when the medical implant 130 is releasably attached to the distal end 116 of the elongate shaft 110.

In some embodiments, the first part 172 of the attachment mechanism 170 and the second part 174 of the attachment mechanism may be configured to interlock with each other such that relative axial translation between the first part 172 of the attachment mechanism 170 and the second part 174 of the attachment mechanism 170 is prevented when the first part 172 of the attachment mechanism 170 abuts the second part 174 of the attachment mechanism 170 and the first longitudinal lumen is aligned coaxially with the second longitudinal lumen. In some embodiments, the first part 172 of the attachment mechanism 170 and the second part 174 of the attachment mechanism 170 are configured to interlock with each other such that relative lateral translation between the first part 172 of the attachment mechanism 170 and the second part 174 of the attachment mechanism 170 is prevented when the first part 172 of the attachment mechanism 170 abuts the second part 174 of the attachment mechanism 170, the first longitudinal lumen is aligned coaxially with the second longitudinal lumen, and the release wire 120 is slidably engaged with the first longitudinal lumen and the second longitudinal lumen.

In some embodiments, a tubular proximal portion 182 of the first part 172 may include an engagement feature configured to non-releasably engage the first part 172 with the elongate shaft 110. Similarly, in some embodiments, a tubular distal portion 184 of the second part 174 may include an engagement feature configured to non-releasably engage the second part 174 with the medical implant 130. In some embodiments, the medical implant system 100 may include the tubular proximal portion 182 of the first part 172 including the engagement feature configured to non-releasably engage the first part 172 with the elongate shaft 110, and the tubular distal portion 184 of the second part 174 including the engagement feature configured to non-releasably engage the second part 174 with the medical implant 130.

In some embodiments, the second part 174 may be formed from a first metallic material, and the medical implant 130 may be formed from a second metallic material dissimilar from the first metallic material. As used herein, "dissimilar" materials may include metals having different metallurgical properties and/or may include different material types. Dissimilar materials may be unsuitable and/or particularly challenging for certain joining processes, such as welding for example. One non-limiting example of dissimilar materials may include nitinol (nickel-titanium alloy) and stainless steel. Similarly, in some embodiments, the first part 172 may be formed from the first metallic material, and the elongate shaft 110 may be formed from the second metallic material or a third metallic material different from the second metallic material. In this context, different materials may be of the same or similar material types but are not necessarily "dissimilar". One non-limiting example of different but not necessarily dissimilar materials may include two different ferrous metals. In some embodiments, the third metallic material may be dissimilar from the first metallic material and/or the second metallic material. In some embodiments, the first metallic material may be substantially identical to the third metallic material. In some embodiments, the second metallic material and/or the third metallic material is a shape memory alloy such as, but not limited to, a nickel-titanium alloy.

In some embodiments, the first part 172 and the second part 174 may be substantially identical. In some embodiments, the first part 172 and the second part 174 may be substantially complimentary to each other. For example, the first part 172 and the second part 174 may have outer surfaces configured to engage with and/or mate to each other when the release wire 120 is in the interlocked position. Several examples of the construction of the first part 172 and/or the second part 174 are described herein. Each example may be used for either or both of the first part 172 and the second part 174 in any given embodiment. In some embodiments, the examples may be intermixed and/or interchanged in any given embodiment. For example, the first part 172 may be constructed differently from the second part 174 while remaining complimentary to each other. In the interest of brevity, each example is described in the singular, but it is to be clearly understood that both the first part 172 and the second part 174, or either of the first part 172 and the second part 174, may be constructed according to the disclosed example(s).

Figure 3:
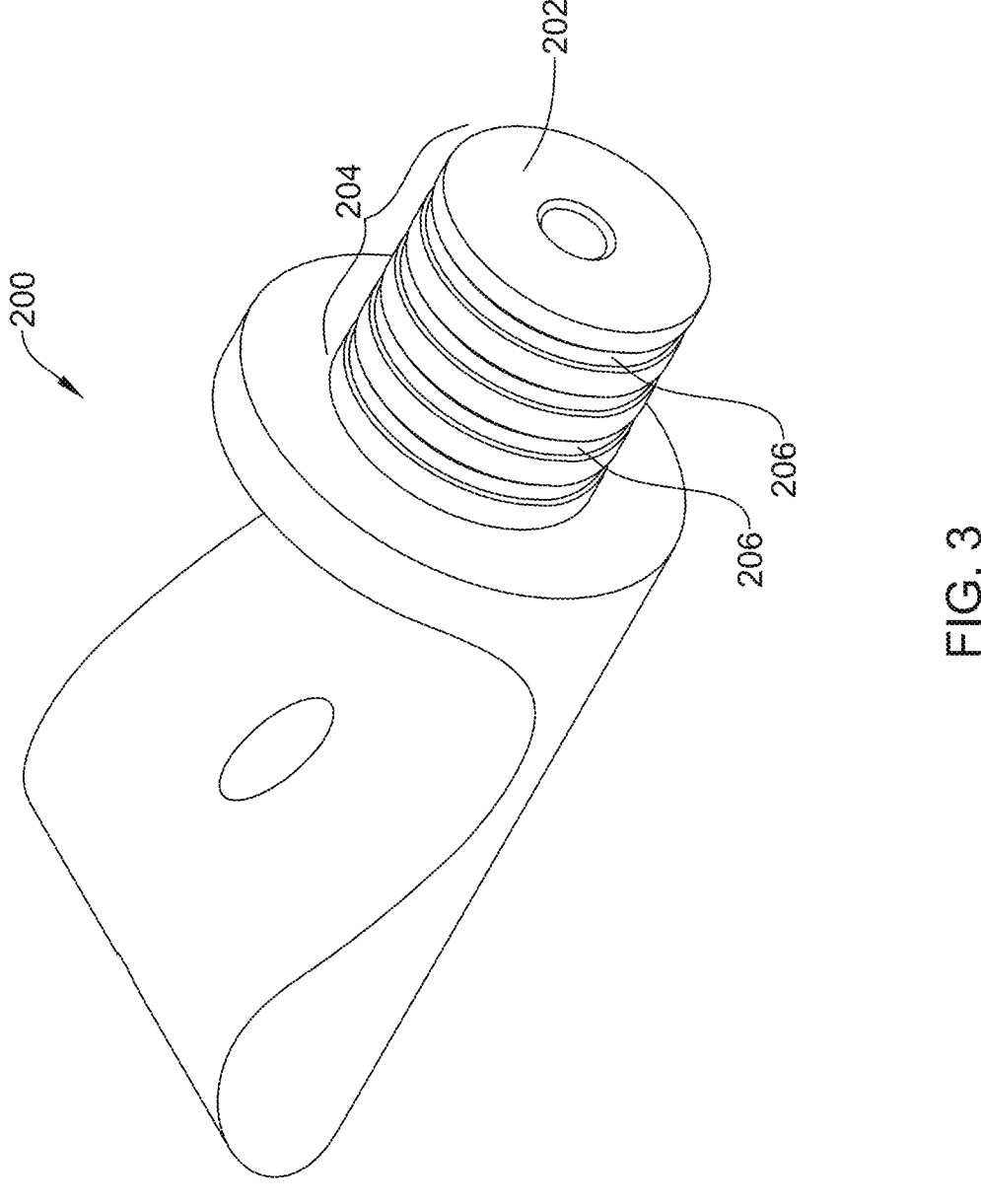
FIG. 3 illustrates a part of an example attachment mechanism.

FIG. 3 illustrates an example first and/or second part 200 that corresponds to and/or may be used in place of the first part 172 and/or the second part 174. The first and/or second part 200 of FIG. 3 may include a tubular portion 202 corresponding to the tubular proximal portion 182 of the first part 172 and/or the tubular distal portion 184 of the second part 174. The tubular (proximal or distal) portion 202 of the first and/or second part 200 may include an engagement feature 204 configured to non-releasably engage the first and/or second part 200 with the elongate shaft 110 and/or the medical implant 130. The engagement feature 204 of the first and/or second part 200 may correspond to the engagement feature of the first part 172 and/or the engagement feature of the second part 174. The engagement feature 204 may include one or more recesses 206 extending into an outer surface of the tubular (proximal or distal) portion 202 of the first and/or second part 200. Some suitable but non-limiting materials for the first and/or second part 200, for example metallic materials, polymer materials, composite materials, etc., are described below.

Figure 4:
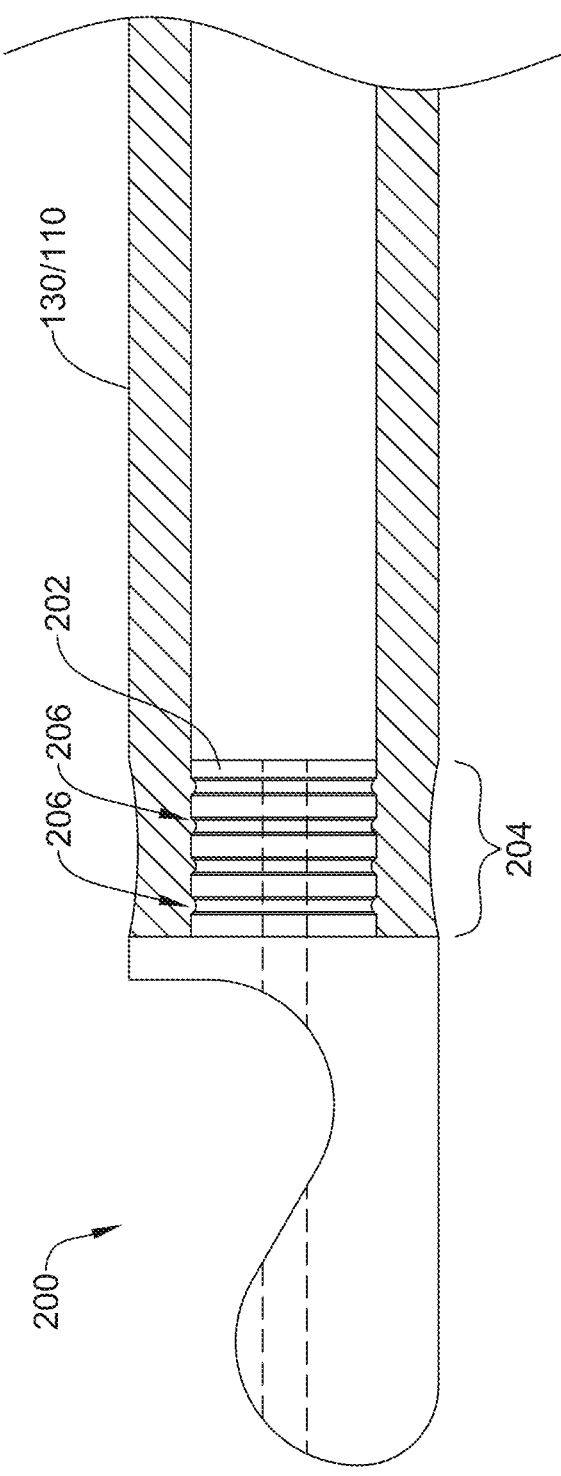
FIG. 4 illustrates attachment of the part of FIG. 3 to an example elongate shaft or medical implant of the example medical implant system.

As shown in FIG. 4, a laser or other suitable heat source may be used to apply heat to the elongate shaft 110 and/or the medical implant 130 to fixedly attach the first and/or second part 200 to the elongate shaft 110 and/or the medical implant 130. Heating the elongate shaft 110 and/or the medical implant 130 may cause melting and/or reflow of the elongate shaft 110 and/or the medical implant 130, wherein a portion of the elongate shaft 110 and/or the medical implant 130 extends into the engagement feature 204 and/or the one or more recesses 206 extending into the outer surface of the tubular (proximal or distal) portion 202 of the first and/or second part 200, thereby creating a mechanical engagement, interference fit, and/or lock fixedly and non-reversibly (e.g., permanently) attaching the first and/or second part 200 to the elongate shaft 110 and/or the medical implant 130. In addition or alternatively, pressure, compression, and/or other means (e.g., swaging, adhesives, chemical dissolution and re-hardening, etc.) may be used to urge and/or cause a portion of the elongate shaft 110 and/or the medical implant 130 to extend into the engagement feature 204 and/or the one or more recesses 206 extending into the outer surface of the tubular (proximal or distal) portion 202 of the first and/or second part 200, thereby creating a mechanical engagement, interference fit, and/or lock fixedly and non-reversibly (e.g., permanently) attaching the first and/or second part 200 to the elongate shaft 110 and/or the medical implant 130.

Figure 5:
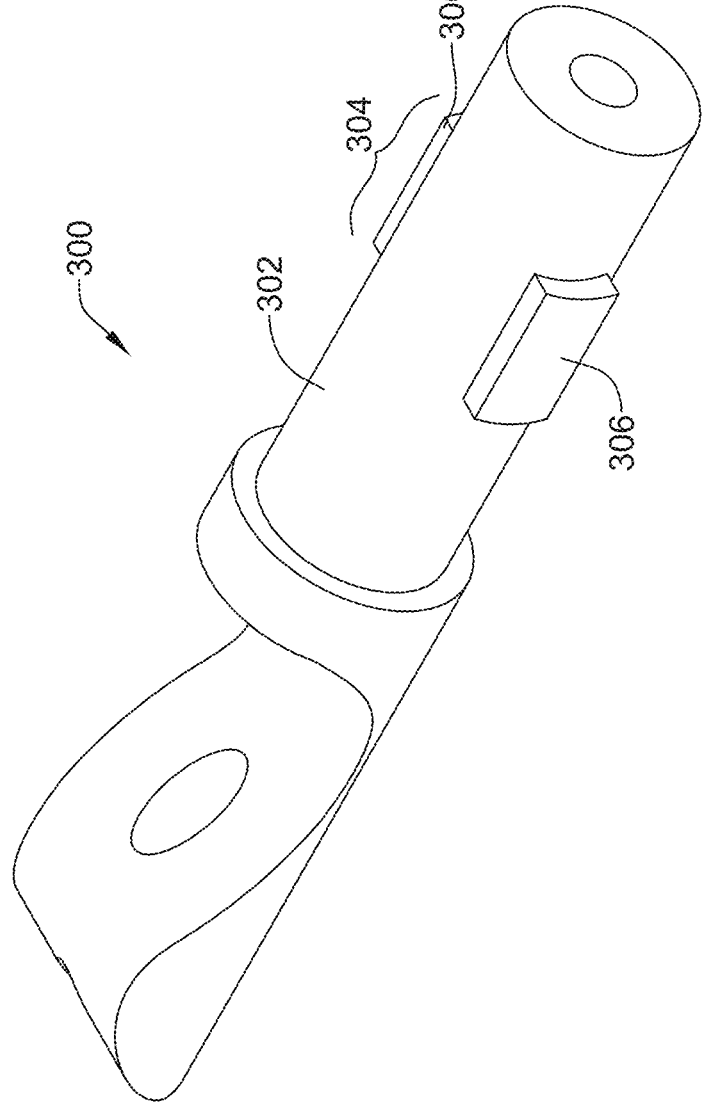
FIG. 5 illustrates a part of an example attachment mechanism.

FIG. 5 illustrates an example first and/or second part 300 that corresponds to and/or may be used in place of the first part 172 and/or the second part 174. The first and/or second part 300 of FIG. 5 may include a tubular portion 302 corresponding to the tubular proximal portion 182 of the first part 172 and/or the tubular distal portion 184 of the second part 174. The tubular (proximal or distal) portion 302 of the first and/or second part 300 may include an engagement feature 304 configured to non-releasably engage the first and/or second part 300 with the elongate shaft 110 and/or the medical implant 130. The engagement feature 304 of the first and/or second part 300 may correspond to the engagement feature of the first part 172 and/or the engagement feature of the second part 174. The engagement feature 304 may include at least one protrusion 306 extending radially outward from an outer surface of the tubular (proximal or distal) portion 302 of the first and/or second part 300. The first and/or second part 300 may be produced using a number of suitable manufacturing means. In one example, the first and/or second part 300 of FIG. 5 may be produced using additive manufacturing techniques. Some suitable but non-limiting materials for the first and/or second part 300, for example metallic materials, polymer materials, composite materials, etc., are described below.

Figure 6:
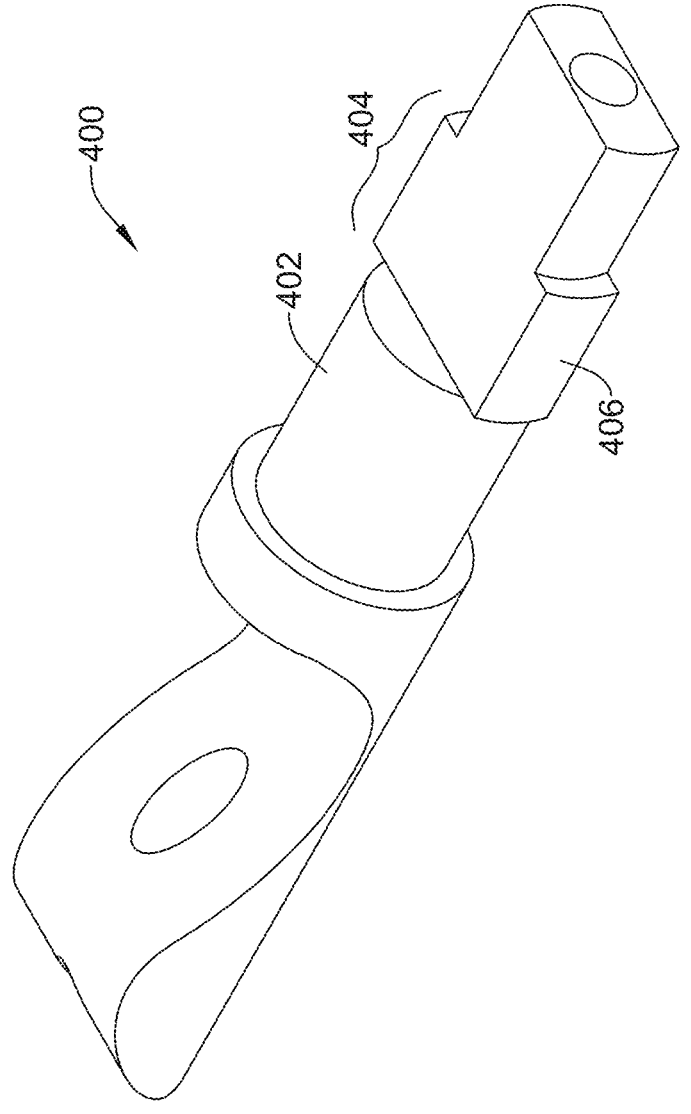
FIG. 6 illustrates a part of an example attachment mechanism.
Figure 6A:
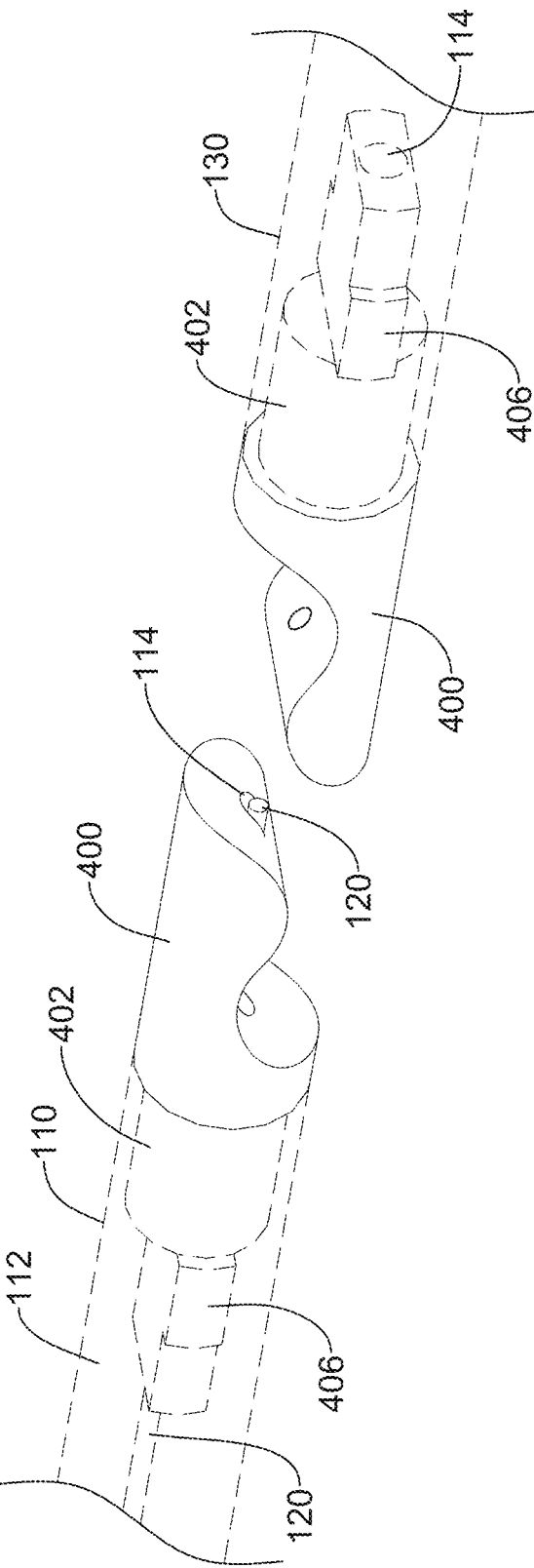
FIG. 6A illustrates an example attachment mechanism.

In another example, a similar first and/or second part 400, shown in FIG. 6, may be produced by machining or other material-removing techniques. The first and/or second part 400 may correspond to and/or may be used in place of the first part 172 and/or the second part 174. The first and/or second part 400 of FIG. 6 may include a tubular portion 402 corresponding to the tubular proximal portion 182 of the first part 172 and/or the tubular distal portion 184 of the second part 174. The tubular (proximal or distal) portion 402 of the first and/or second part 400 may include an engagement feature 404 configured to non-releasably engage the first and/or second part 400 with the elongate shaft 110 and/or the medical implant 130. The engagement feature 404 of the first and/or second part 400 may correspond to the engagement feature of the first part 172 and/or the engagement feature of the second part 174. The engagement feature 404 may include at least one protrusion 406 extending radially outward from an outer surface of the tubular (proximal or distal) portion 402 of the first and/or second part 400. In some embodiments, manufacture of the at least one protrusion 406 may remove a portion of the tubular (proximal or distal) portion 402 of the first and/or second part 400 to define one or more substantially flat faces, as seen in FIG. 6. FIG. 6A illustrates two of the first and/or second parts 400 of the attachment mechanism of FIG. 6 engaged with the elongate shaft 110 and medical implant 130 of the medical implant system shown in FIG. 1. Each of the first and/or second parts 400 includes a lumen 114 through which the release wire 120 may extend. FIG. 6A depicts the medical implant system following release of the medical implant 130. Some suitable but non-limiting materials for the first and/or second part 400, for example metallic materials, polymer materials, composite materials, etc., are described below.

Figure 7:
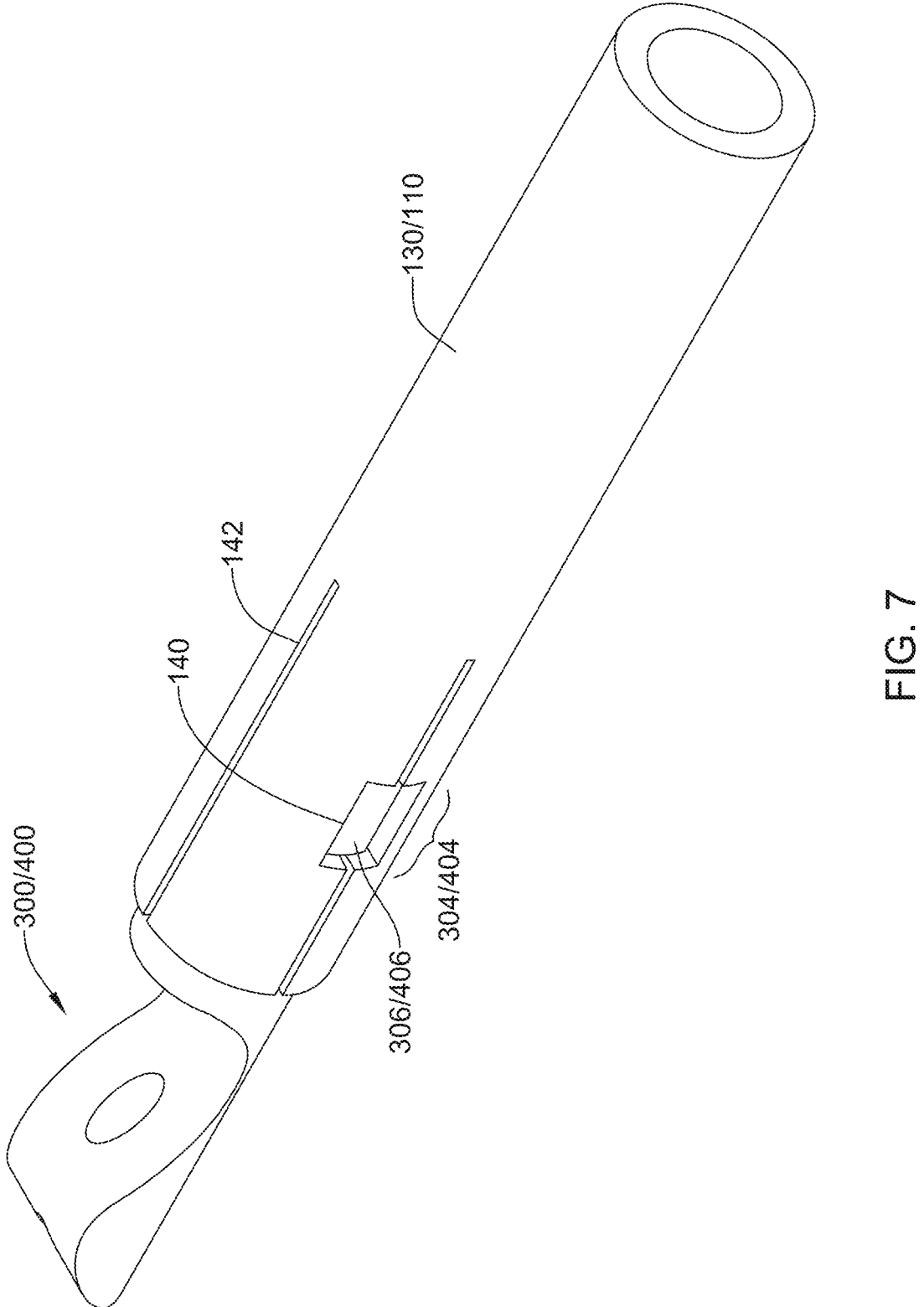
FIGS. 7-9 illustrate attachment of the parts of FIGS. 5 and 6 to an example elongate shaft or medical implant of the example medical implant system.
Figure 8:
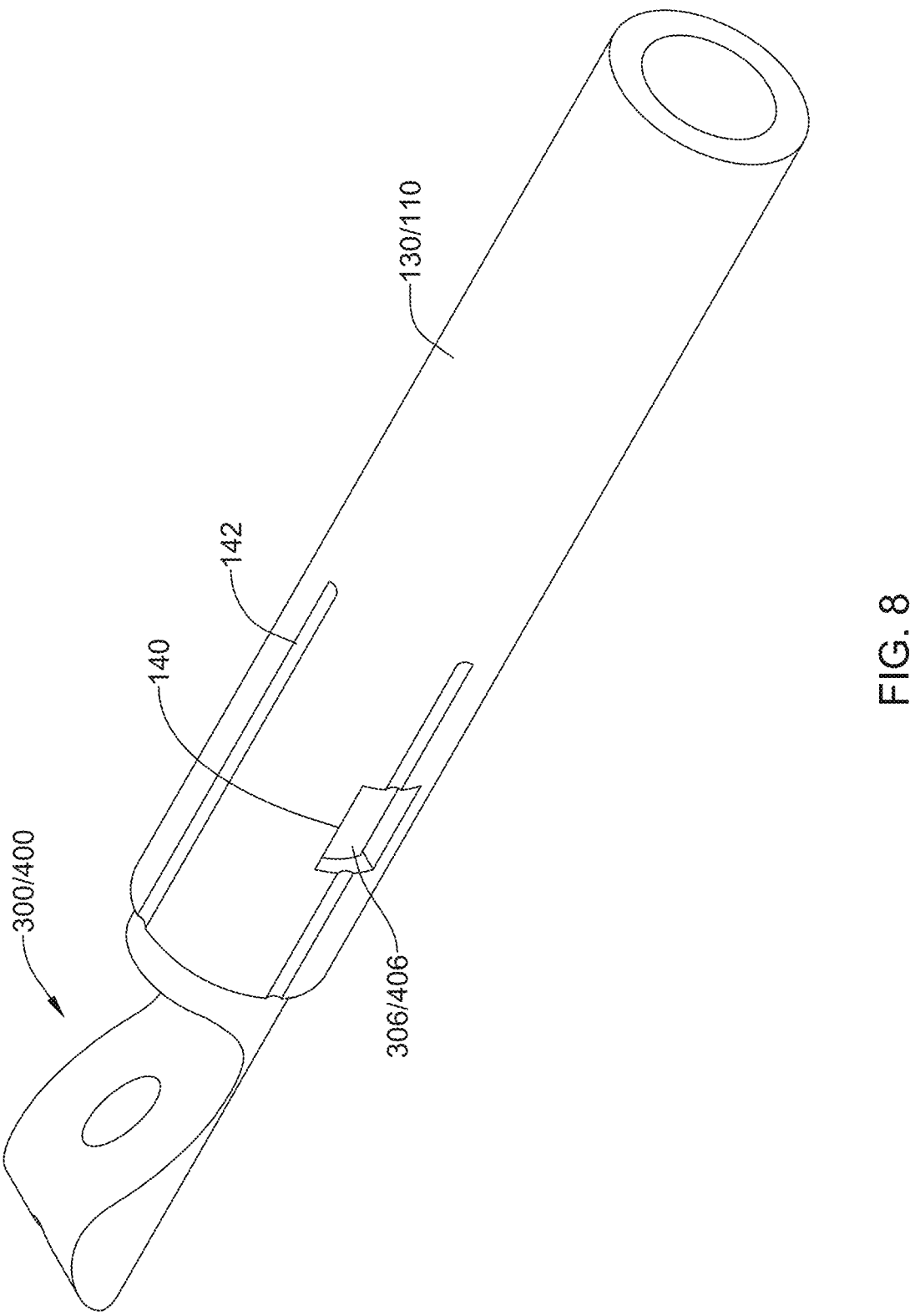
Figure 9:
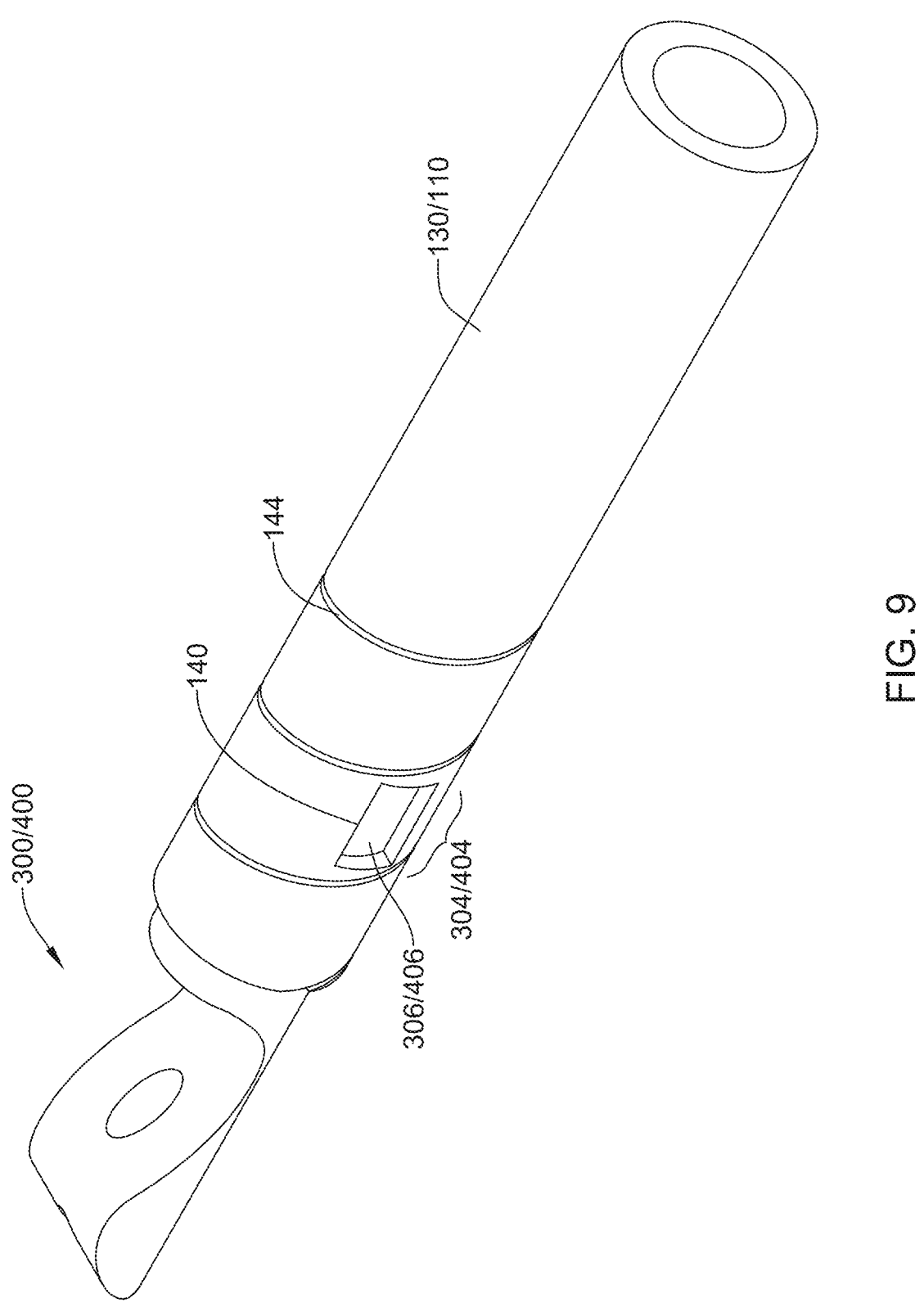

FIGS. 7-9 illustrate attachment of the example first and/or second part 300 and/or the example first and/or second part 400 to the elongate shaft 110 and/or the medical implant 130. In some embodiments, the elongate shaft 110 and/or the medical implant 130 may include at least one window 140 extending through a wall of the elongate shaft 110 and/or the medical implant 130 configured to receive the at least one protrusion 306/406. In some embodiments, the elongate shaft 110 and/or the medical implant 130 may include at least one longitudinally-oriented and/or radially-oriented cut 142 extending away from an end of the elongate shaft 110 and/or the medical implant 130 (e.g., extending proximally from a distal end of the elongate shaft 110, extending distally from a proximal end of the medical implant 130). The at least one longitudinally-oriented and/or radially-oriented cut 142 may permit flexure of the elongate shaft 110 and/or the medical implant 130 over the at least one protrusion 306/406, thereby facilitating assembly of the first and/or second part 300/400 and the elongate shaft 110 and/or the medical implant 130. Material on opposing sides of the at least one longitudinally-oriented and/or radially-oriented cut 142 may be fixedly secured together after the tubular (proximal or distal) portion 302/402 is inserted into the proximal end of the medical implant 130 and/or the distal end of the elongate shaft 110.

After seating the at least one protrusion 306/406 into the at least one window 140, as shown in FIG. 7 for example, heat may be applied to the elongate shaft 110 and/or the medical implant 130, such as with a laser, a welder, or other suitable means. In at least some embodiments, applying heat to the elongate shaft 110 and/or the medical implant 130 may include welding (e.g., seam welding, spot welding, etc.) the elongate shaft 110 and/or the medical implant 130 to itself along each of the at least one longitudinally-oriented and/or radially-oriented cut 142, shown at least partially filled-in (e.g., welded) in FIG. 8 for example, thereby creating a mechanical engagement, interference fit, and/or lock fixedly and non-reversibly (e.g., permanently) attaching the first and/or second part 300/400 to the elongate shaft 110 and/or the medical implant 130. In addition or alternatively, pressure, compression, and/or other means (e.g., swaging, adhesives, chemical dissolution and re-hardening, etc.) may be used to fixedly secure material on opposing sides of the at least one longitudinally-oriented and/or radially-oriented cut 142 after the tubular (proximal or distal) portion 302/402 is inserted into the proximal end of the medical implant 130 and/or the distal end of the elongate shaft 110, thereby creating a mechanical engagement, interference fit, and/or lock fixedly and non-reversibly (e.g., permanently) attaching the first and/or second part 200 to the elongate shaft 110 and/or the medical implant 130.

In an alternative configuration, shown in FIG. 9 for example, the elongate shaft 110 and/or the medical implant 130 may include a helical and/or radial-oriented cut 144 extending away from an end of the elongate shaft 110 and/or the medical implant 130 (e.g., extending proximally from a distal end of the elongate shaft 110, extending distally from a proximal end of the medical implant 130). The helical and/or radially-oriented cut 144 may permit flexure of the elongate shaft 110 and/or the medical implant 130 over the at least one protrusion 306/406, thereby facilitating assembly of the first and/or second part 300/400 and the elongate shaft 110 and/or the medical implant 130. Material on opposing sides of the helical and/or radially-oriented cut 142 may be fixedly secured together after the tubular (proximal or distal) portion 302/402 is inserted into the proximal end of the medical implant 130 and/or the distal end of the elongate shaft 110, using any of the methods and/or means discussed above with respect to at least one longitudinally-oriented and/or radially-oriented cut 142.

Figure 10:
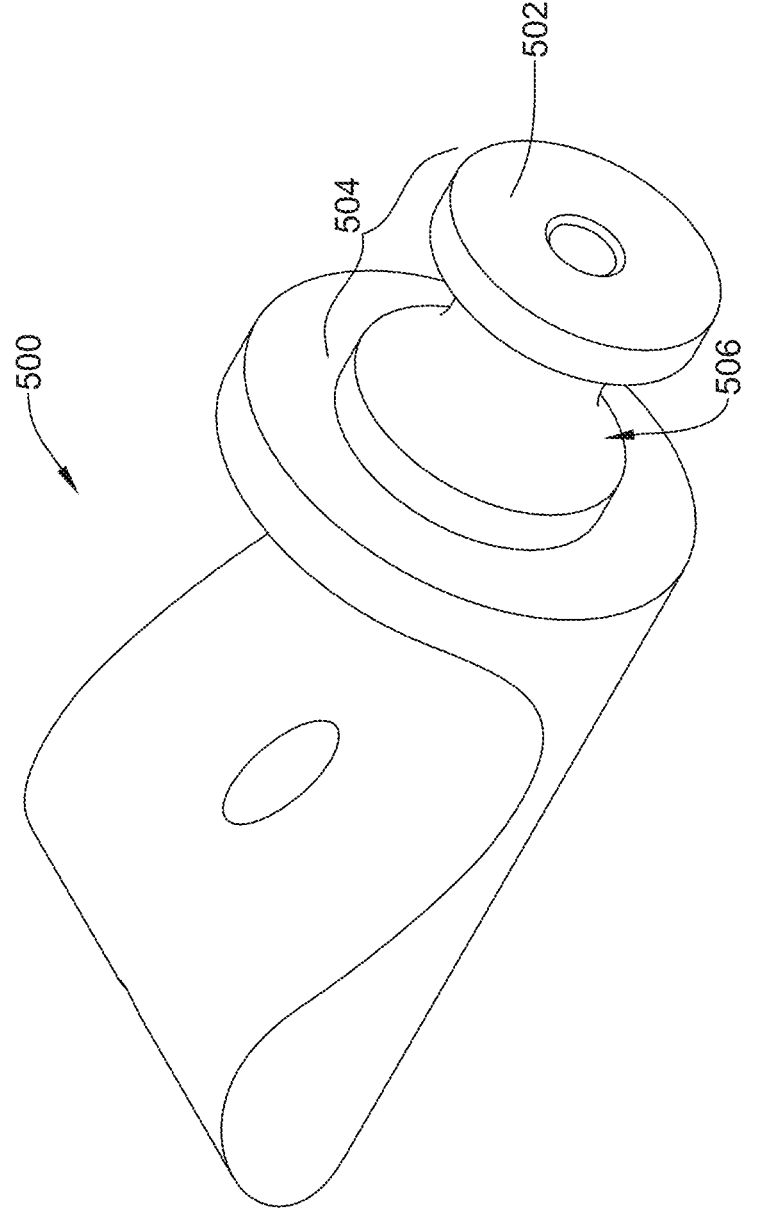
FIG. 10 illustrates a part of an example attachment mechanism.

FIG. 10 illustrates an example first and/or second part 500 that corresponds to and/or may be used in place of the first part 172 and/or the second part 174. The first and/or second part 500 of FIG. 10 may include a tubular portion 502 corresponding to the tubular proximal portion 182 of the first part 172 and/or the tubular distal portion 184 of the second part 174. The tubular (proximal or distal) portion 502 of the first and/or second part 500 may include an engagement feature 504 configured to non-releasably engage the first and/or second part 500 with the elongate shaft 110 and/or the medical implant 130. The engagement feature 504 of the first and/or second part 500 may correspond to the engagement feature of the first part 172 and/or the engagement feature of the second part 174. The engagement feature 504 may include one or more recesses 506 extending into an outer surface of the tubular (proximal or distal) portion 502 of the first and/or second part 500. In one example, the one or more recesses 506 may include and/or define an hourglass shape extending radially inward from the outer surface of the tubular (proximal or distal) portion 502 of the first and/or second part 500. Some suitable but non-limiting materials for the first and/or second part 500, for example metallic materials, polymer materials, composite materials, etc., are described below.

Figure 11:
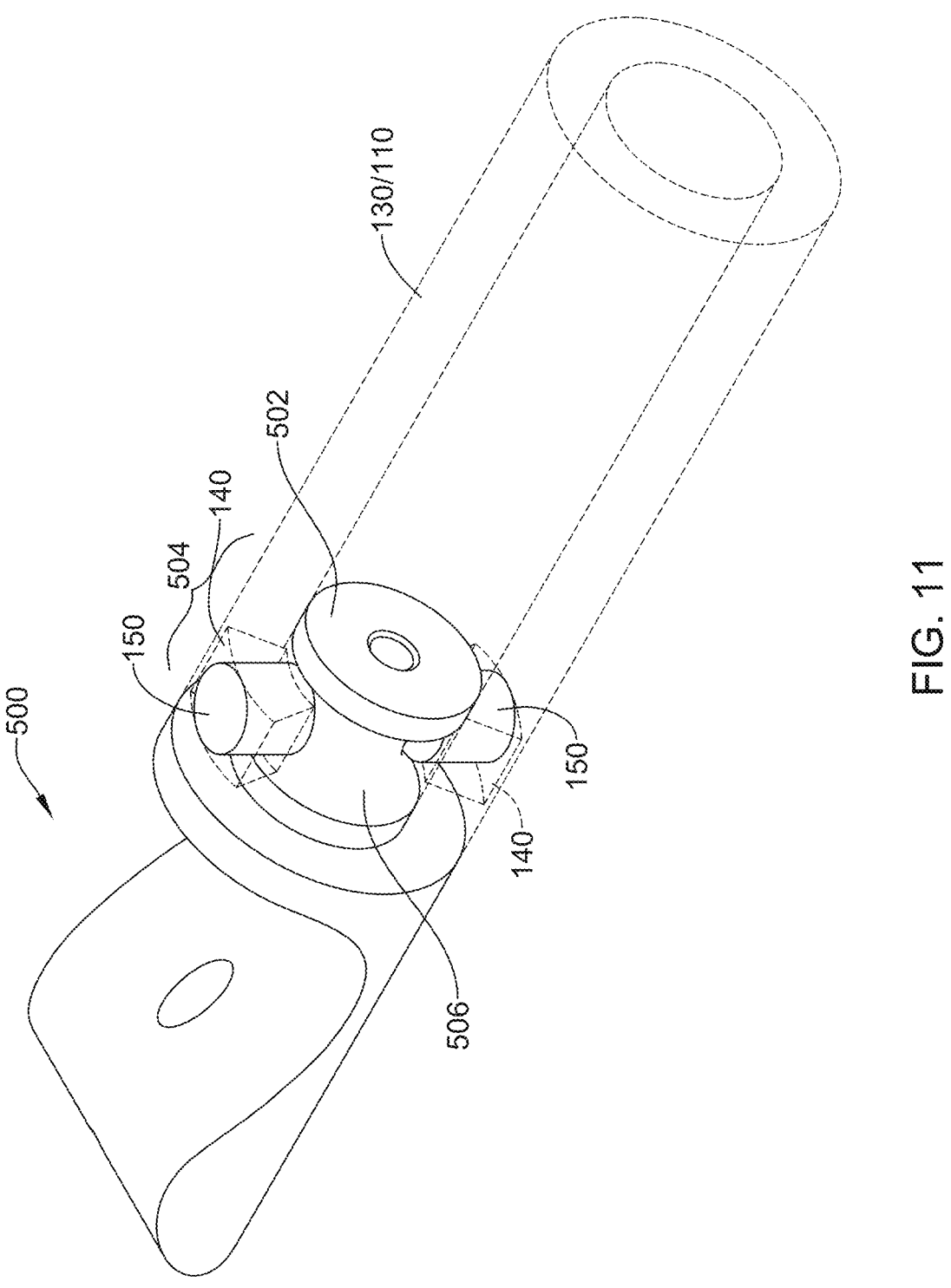
FIGS. 11 and 12 illustrate attachment of the part of FIG. 10 to an example elongate shaft or medical implant of the example medical implant system.
Figure 12:
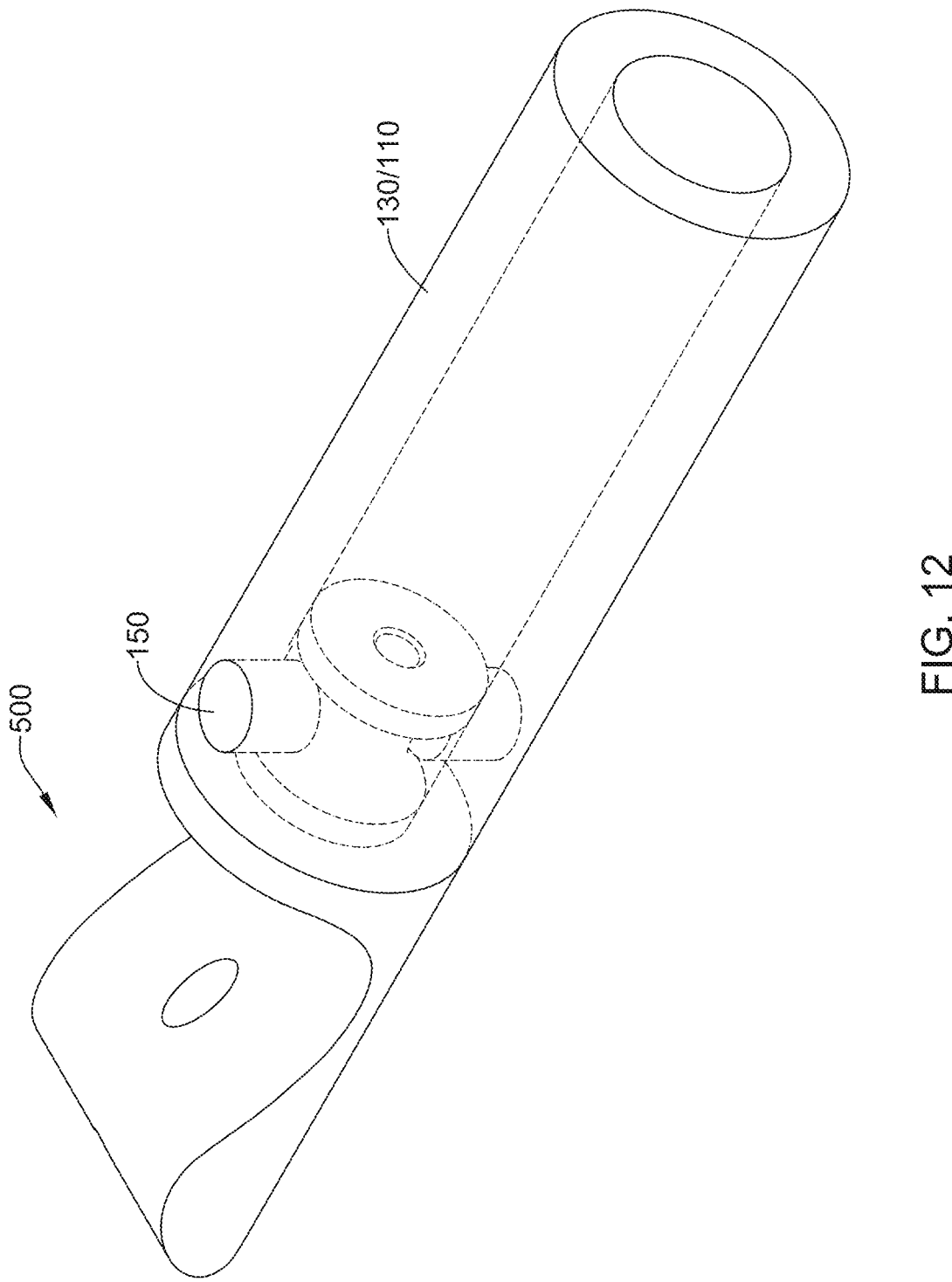

Turning now to FIGS. 11 and 12, certain features are shown using hidden or phantom lines to ease understanding of the features and their relationships to each other, and such illustration is not intended to be limiting. As shown in FIG. 11, at least one plug 150 may each be inserted through at least one window 140 in the elongate shaft 110 and/or the medical implant 130. The at least one plug 150 may be fixedly attached to the elongate shaft 110 and/or the medical implant 130 after the at least one plug 150 is inserted through the at least one window 140. For example, a laser or other suitable heat source may be used to apply heat to the at least one plug 150 and/or the elongate shaft 110 and/or the medical implant 130 to fixedly attach the first and/or second part 500 to the elongate shaft 110 and/or the medical implant 130. Heating the at least one plug 150 and/or the elongate shaft 110 and/or the medical implant 130 may cause melting and/or reflow of the at least one plug 150 and/or the elongate shaft 110 and/or the medical implant 130, wherein a portion of the at least one plug 150 and/or the elongate shaft 110 and/or the medical implant 130 extends into the engagement feature 504 and/or the one or more recesses 506 extending into the outer surface of the tubular (proximal or distal) portion 502 of the first and/or second part 500, thereby creating a mechanical engagement, interference fit, and/or lock fixedly and non-reversibly (e.g., permanently) attaching the first and/or second part 500 to the elongate shaft 110 and/or the medical implant 130, as shown in FIG. 12 for example, thereby creating a mechanical engagement, interference fit, and/or lock fixedly and non-reversibly (e.g., permanently) attaching the first and/or second part 500 to the elongate shaft 110 and/or the medical implant 130. In at least some embodiments, melting and/or reflow of the at least one plug 150 and/or the elongate shaft 110 and/or the medical implant 130 may cause the at least one plug 150 to become an integral part of the elongate shaft 110 and/or the medical implant 130, wherein after heating, melting, and/or reflow, a portion of the elongate shaft 110 and/or the medical implant 130 extends into the one or more recesses 506 extending into the outer surface of the tubular (proximal or distal) portion 502 of the first and/or second part 500. In addition or alternatively, pressure, compression, and/or other means (e.g., swaging, adhesives, chemical dissolution and re-hardening, etc.) may be used to fixedly and non-reversibly (e.g., permanently) attach the first and/or second part 500 to the elongate shaft 110 and/or the medical implant 130.

Figure 13:
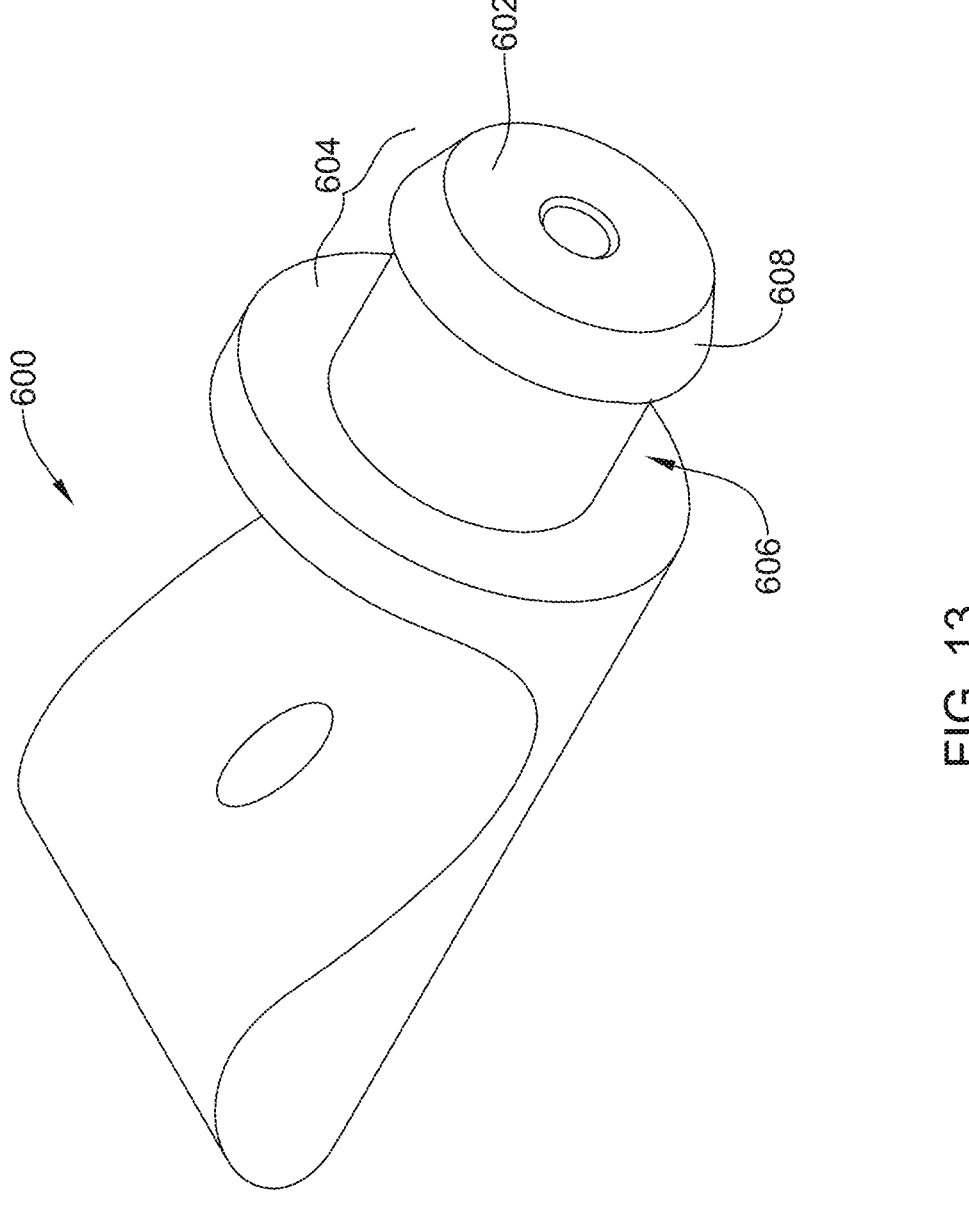
FIG. 13 illustrates a part of an example attachment mechanism.

FIG. 13 illustrates an example first and/or second part 600 that corresponds to and/or may be used in place of the first part 172 and/or the second part 174. The first and/or second part 600 of FIG. 13 may include a tubular portion 602 corresponding to the tubular proximal portion 182 of the first part 172 and/or the tubular distal portion 184 of the second part 174. The tubular (proximal or distal) portion 602 of the first and/or second part 600 may include an engagement feature 604 configured to non-releasably engage the first and/or second part 600 with the elongate shaft 110 and/or the medical implant 130. The engagement feature 604 of the first and/or second part 600 may correspond to the engagement feature of the first part 172 and/or the engagement feature of the second part 174. The engagement feature 604 may include one or more recesses 606 extending into an outer surface of the tubular (proximal or distal) portion 602 of the first and/or second part 600. Alternatively, the engagement feature 604 may include at least one protrusion 608 extending radially outward from the tubular (proximal or distal) portion 602 of the first and/or second part 600. In some embodiments, the engagement feature 604 may include both the one or more recesses 606 extending into the outer surface of the tubular (proximal or distal) portion 602 of the first and/or second part 600 and the at least one protrusion 608 extending radially outward from the tubular (proximal or distal) portion 602 of the first and/or second part 600. Some suitable but non-limiting materials for the first and/or second part 600, for example metallic materials, polymer materials, composite materials, etc., are described below.

Figure 14:
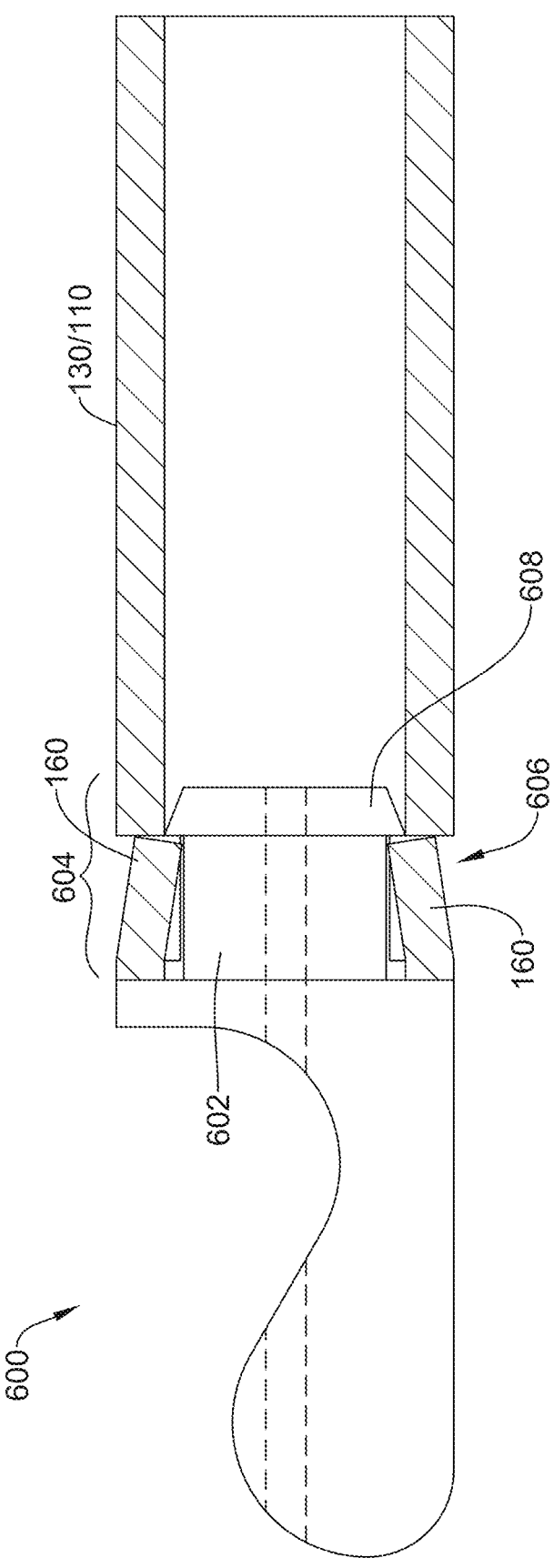
FIGS. 14 and 15 illustrate attachment of the part of FIG. 13 to an example elongate shaft or medical implant of the example medical implant system.
Figure 15:
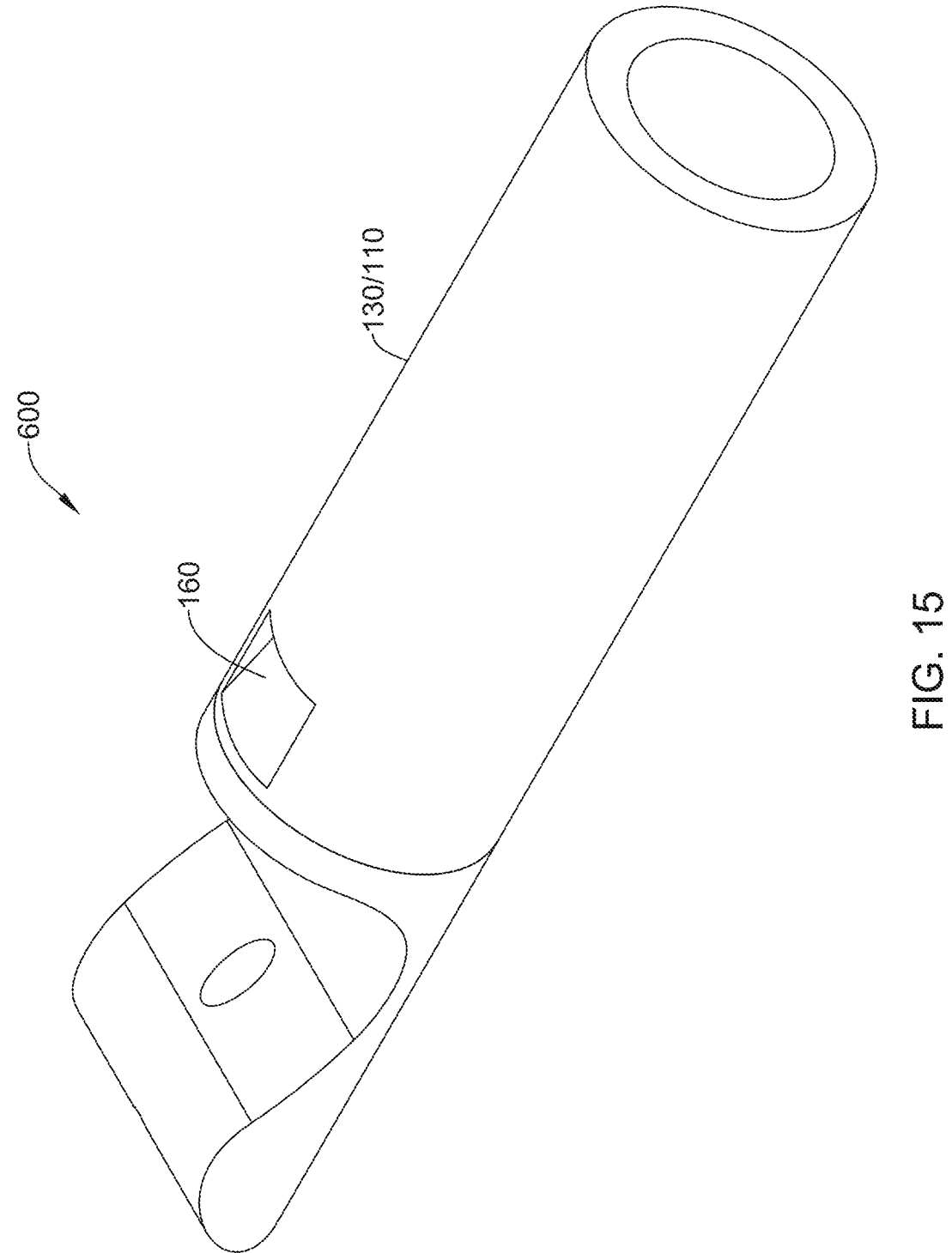

As shown in FIGS. 14 and 15, a portion of the elongate shaft 110 and/or the medical implant 130 may extend into the one or more recesses 606 extending into the outer surface of the tubular (proximal or distal) portion 602 of the first and/or second part 600 and/or the portion of the elongate shaft 110 and/or the medical implant 130 may engage against the at least one protrusion 608 extending radially outward from the tubular (proximal or distal) portion 602 of the first and/or second part 600, after the tubular (proximal or distal) portion 602 of the first and/or second part 600 is inserted into the distal end 116 of the elongate shaft 110 and/or the proximal end of the medical implant 130, thereby preventing withdrawal of the tubular (proximal or distal) portion 602 of the first and/or second part 600 from the distal end 116 of the elongate shaft 110 and/or the proximal end of the medical implant 130.

In some embodiments, the portion of the elongate shaft 110 and/or the medical implant 130 extending into the one or more recesses 606 extending into the outer surface of the tubular (proximal or distal) portion 602 of the first and/or second part 600 may include a moveable tab 160 biased radially inward. In at least some embodiments, the moveable tab 160 may be self-biased radially inward. In some embodiments, the moveable tab 160 may include a plurality of moveable tabs (e.g., two moveable tabs, three moveable tabs, four moveable tabs, etc.). As such, when the tubular (proximal or distal) portion 602 of the first and/or second part 600 is inserted into the distal end 116 of the elongate shaft 110 and/or the proximal end of the medical implant 130, the tubular (proximal or distal) portion 602 of the first and/or second part 600 and/or the at least one protrusion 608 extending radially outward from the tubular (proximal or distal) portion 602 of the first and/or second part 600 may deflect the moveable tab 160 radially outward until the moveable tab 160 reaches the one or more recesses 606 extending into the outer surface of the tubular (proximal or distal) portion 602 of the first and/or second part 600, at which time, the moveable tab 160 will be biased radially inward into the one or more recesses 606 extending into the outer surface of the tubular (proximal or distal) portion 602 of the first and/or second part 600, thereby creating a mechanical engagement, interference fit, and/or lock fixedly and non-reversibly (e.g., permanently) attaching the first and/or second part 600 to the elongate shaft 110 and/or the medical implant 130.

In conjunction with the discussion herein, a method of making the medical implant system 100 may comprise: inserting the first part 172 (e.g., the first and/or second part 200, 300, 400, 500, 600) of the attachment mechanism 170 into the distal end 116 of the elongate shaft 110 and securing the first part 172 (e.g., the first and/or second part 200, 300, 400, 500, 600) of the attachment mechanism 170 to the elongate shaft 110; inserting the second part 174 (e.g., the first and/or second part 200, 300, 400, 500, 600) of the attachment mechanism 170 into the proximal end of the medical implant 130, wherein the second part 174 (e.g., the first and/or second part 200, 300, 400, 500, 600) of the attachment mechanism 170 is formed from a first metallic material and the medical implant 130 is formed from a second metallic material dissimilar from the first metallic material; and applying heat to the elongate shaft 110 and/or the medical implant 130 to fixedly attach the first part 172 (e.g., the first and/or second part 200, 300, 400, 500, 600) of the attachment mechanism 170 to the elongate shaft 110 and/or the second part 174 (e.g., the first and/or second part 200, 300, 400, 500, 600) of the attachment mechanism 170 to the medical implant 130. In some embodiments, the elongate shaft 110 and/or the medical implant 130 may be formed from a shape memory alloy such as, but not limited to, a nickel-titanium alloy. In addition or alternatively, the method may include applying pressure, compression, and/or other means (e.g., swaging, adhesives, chemical dissolution and re-hardening, etc.) to the elongate shaft 110 and/or the medical implant 130 to fixedly attach the first part 172 (e.g., the first and/or second part 200, 300, 400, 500, 600) of the attachment mechanism 170 to the elongate shaft 110 and/or the second part 174 (e.g., the first and/or second part 200, 300, 400, 500, 600) of the attachment mechanism 170 to the medical implant 130.

In some embodiments, applying heat to the elongate shaft 110 and/or the medical implant 130 may cause a portion of the elongate shaft 110 and/or the medical implant 130 to reflow into one or more recesses extending into the outer surface of the first part 172 (e.g., the first and/or second part 200, 300, 400, 500, 600) of the attachment mechanism 170 and/or the second part 174 (e.g., the first and/or second part 200, 300, 400, 500, 600) of the attachment mechanism 170. In some embodiments, applying heat to the elongate shaft 110 and/or the medical implant 130 includes welding (e.g., seam welding, spot welding, etc.) the elongate shaft 110 and/or the medical implant 130 to itself, and/or reflowing the elongate shaft 110 and/or the medical implant 130. In some embodiments, applying heat to the elongate shaft 110 and/or the medical implant 130 includes heating a plug 150 inserted through a window 140 in the elongate shaft 110 and/or the medical implant 130 such that the plug 150 reflows with the elongate shaft 110 and/or the medical implant 130 and becomes integrated with the elongate shaft 110 and/or the medical implant 130. In addition or alternatively, pressure, compression, and/or other means (e.g., swaging, adhesives, chemical dissolution and re-hardening, etc.) may be used to fixedly attach the second part 174 (e.g., the first and/or second part 200, 300, 400, 500, 600) of the attachment mechanism 170 to the medical implant 130, and/or the first part 172 (e.g., the first and/or second part 200, 300, 400, 500, 600) of the attachment mechanism 170 to the elongate shaft 110.

In some embodiments, the method may further comprise applying heat, pressure, compression, and/or other means (e.g., swaging, adhesives, chemical dissolution and re-hardening, etc.) to the distal end 116 of the elongate shaft 110 to fixedly attach the first part 172 (e.g., the first and/or second part 200, 300, 400, 500, 600) of the attachment mechanism 170 to the distal end 116 of the elongate shaft 110. In some embodiments, the first part 172 (e.g., the first and/or second part 200, 300, 400, 500, 600) of the attachment mechanism 170 is formed from the first metallic material and the elongate shaft 110 is formed from a third metallic material dissimilar from the first metallic material. In some embodiments, the third metallic material is a shape memory alloy such as, but not limited to, a nickel-titanium alloy.

In use, a method of delivering the medical implant 130 to a treatment site (e.g., a vein, an artery, etc.) may include inserting the microcatheter into a patient's anatomy and guiding the distal end of the microcatheter to a location adjacent the treatment site. The method may include inserting the medical implant 130 disposed at and/or proximate the distal end 116 of the elongate shaft 110 into a proximal end of the lumen disposed within the microcatheter. In some embodiments, the medical implant 130 may be inserted into the lumen of the microcatheter after the microcatheter is inserted into the patient's anatomy. The method may include advancing the medical implant 130 through the microcatheter to the treatment site. The medical implant 130 may be releasably attached to the distal end 116 of the elongate shaft 110 by the release wire 120 extending through the lumen 112 within the elongate shaft 110. The securement member may extend proximally from the elongate shaft 110, and the securement member may be fixedly attached to the elongate shaft 110 and the release wire 120. Alternatively, in some embodiments, the medical implant 130 may be inserted into the proximal end of the lumen of the microcatheter and advanced through the microcatheter to a distal end of the microcatheter before the microcatheter is inserted into the patient's anatomy.

As discussed herein, the proximal portion of the securement member may be fixedly attached to a proximal end of the release wire 120 and the distal portion of the securement member may be fixedly attached to the proximal end of the elongate shaft 110. The first part 172 of the attachment mechanism 170 may be attached to the distal end 116 of the elongate shaft 110, and the second part 174 of the attachment mechanism 170 may be fixedly attached to a proximal end of the medical implant 130. The release wire 120 may be slidably disposed within a lumen of the distal portion of the securement member, the lumen 112 of the elongate shaft 110, the first longitudinal lumen of the first part 172 of the attachment mechanism 170, and the second longitudinal lumen of the second part 174 of the attachment mechanism 170.

The method may include translating the proximal portion of the securement member proximally away from the proximal end of the elongate shaft 110 while the elongate shaft 110 is maintained in a fixed position with respect to the treatment site to translate the release wire 120 relative to the elongate shaft 110 and/or the attachment mechanism 170 to shift the release wire 120 from an interlocked position to a released position, thereby releasing the medical implant 130 from the elongate shaft 110.

The method may also include proximal withdrawal of the elongate shaft 110 and/or the microcatheter from the treatment site. For example, in some embodiments, the elongate shaft 110 may be withdrawn proximally through the lumen of the microcatheter and removed, and the microcatheter may then be withdrawn and/or removed from the patient's anatomy. In some embodiments, the elongate shaft 110 may be withdrawn proximally far enough for the distal end 116 of the elongate shaft 110 and/or the first part 172 of the attachment mechanism 170 to be positioned within the distal end and/or the lumen of the microcatheter. The elongate shaft 110 and the microcatheter may then be withdrawn together from the patient's anatomy.

In some embodiments, the elongate shaft 110 may be removed through the lumen of the microcatheter, and the microcatheter may be left and/or held in place within the patient's anatomy. If needed, a second elongate shaft and associated second medical device may then be inserted into the proximal end of the lumen of the microcatheter and advanced to the treatment site for deployment. Additional repetitions of the device(s) described herein, as well as the described method steps, may be used as needed or desired for a particular procedure.

The materials that can be used for the various components of the medical implant system 100, the elongate shaft 110, the release wire 120, the medical implant 130, the at least one plug 150, the attachment mechanism 170, the microcatheter, the first and/or second part 200/300/400/500/600, etc. (and/or other systems disclosed herein) and the various elements thereof disclosed herein may include those commonly associated with medical devices. For simplicity purposes, the following discussion makes reference to the medical implant system 100, the elongate shaft 110, the release wire 120, the medical implant 130, the at least one plug 150, the attachment mechanism 170, the microcatheter, the first and/or second part 200/300/400/500/600, etc. However, this is not intended to limit the devices and methods described herein, as the discussion may be applied to other elements, members, components, or devices disclosed herein, such as, but not limited to, the first part 172, the second part 174, the tubular proximal portion 182, the tubular distal portion 184, the tubular (proximal or distal) portion 202/302/402/502/602, the engagement feature 204/304/404/504/604, the at least one protrusion 306/406/608, etc. and/or elements or components thereof.

In some embodiments, the medical implant system 100, the elongate shaft 110, the release wire 120, the medical implant 130, the at least one plug 150, the attachment mechanism 170, the microcatheter, the first and/or second part 200/300/400/500/600, etc., and/or components thereof (such as, but not limited to, the first part 172, the second part 174, the tubular proximal portion 182, the tubular distal portion 184, the tubular (proximal or distal) portion 202/302/402/502/602, the engagement feature 204/304/404/504/604, the at least one protrusion 306/406/608, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as but not limited to 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical implant system 100, the elongate shaft 110, the release wire 120, the medical implant 130, the at least one plug 150, the attachment mechanism 170, the microcatheter, the first and/or second part 200/300/400/500/600, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical implant system 100, the elongate shaft 110, the release wire 120, the medical implant 130, the at least one plug 150, the attachment mechanism 170, the microcatheter, the first and/or second part 200/300/400/500/600, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical implant system 100, the elongate shaft 110, the release wire 120, the medical implant 130, the at least one plug 150, the attachment mechanism 170, the microcatheter, the first and/or second part 200/300/400/500/600, etc. to achieve the same result.

In some embodiments, a degree of Magnetic Resonance Imaging (MM) compatibility is imparted into the medical implant system 100, the elongate shaft 110, the release wire 120, the medical implant 130, the at least one plug 150, the attachment mechanism 170, the microcatheter, the first and/or second part 200/300/400/500/600, etc. For example, the medical implant system 100, the elongate shaft 110, the release wire 120, the medical implant 130, the at least one plug 150, the attachment mechanism 170, the microcatheter, the first and/or second part 200/300/400/500/600, etc., and/or components or portions thereof, may be made of a material that does not substantially distort the image and create substantial artifacts (e.g., gaps in the image). Certain ferromagnetic materials, for example, may not be suitable because they may create artifacts in an MM image. The medical implant system 100, the elongate shaft 110, the release wire 120, the medical implant 130, the at least one plug 150, the attachment mechanism 170, the microcatheter, the first and/or second part 200/300/400/500/600, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical implant system 100, the elongate shaft 110, the release wire 120, the medical implant 130, the at least one plug 150, the attachment mechanism 170, the microcatheter, the first and/or second part 200/300/400/500/600, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical implant system 100, the elongate shaft 110, the release wire 120, the medical implant 130, the at least one plug 150, the attachment mechanism 170, the microcatheter, the first and/or second part 200/300/400/500/600, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical implant system 100, the elongate shaft 110, the release wire 120, the medical implant 130, the at least one plug 150, the attachment mechanism 170, the microcatheter, the first and/or second part 200/300/400/500/600, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical implant system 100, the elongate shaft 110, the release wire 120, the medical implant 130, the at least one plug 150, the attachment mechanism 170, the microcatheter, the first and/or second part 200/300/400/500/600, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasa-lazine, and mesalamine); antineoplastic/antiproliferative/anti-mitotic agents (such as paclitaxel, 5-fluorouracil, cis-platin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspi-rin, prostaglandin inhibitors, platelet inhibitors, and tick antiplatelet peptides); vascular cell growth promoters (such as growth factor inhibitors, growth factor receptor antago-nists, transcriptional activators, and translational promot-ers); vascular cell growth inhibitors (such as growth factor inhibitors, growth factor receptor antagonists, transcrip-tional repressors, translational repressors, replication inhibi-tors, inhibitory antibodies, antibodies directed against growth factors, bifunctional molecules consisting of a growth factor and a cytotoxin, bifunctional molecules con-sisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed:

1. A system comprising:
an elongate shaft including a wall defining a lumen;
a medical implant including a wall defining a lumen;
a first attachment part configured to be fixedly attached to a distal end of the elongate shaft, the first attachment part having a tubular proximal portion with a first engagement feature configured to non-reversibly engage the elongate shaft, such that when the tubular proximal portion and the first engagement feature are inserted within the lumen of the elongate shaft, the first engagement feature fixedly attaches the first attachment part to the elongate shaft; and
a second attachment part configured to be fixedly attached to a proximal end of the medical implant, the second attachment part having a tubular distal portion with a second engagement feature configured to non-revers-ibly engage the medical implant, thereby fixedly attach-ing the second attachment part to the medical implant;
wherein the first attachment part and the second attach-ment part are configured to interlock with each other such that relative axial translation between the first attachment part and the second attachment part is prevented when the first attachment part is interlocked with the second attachment part;
wherein the tubular distal portion and the second engage-ment feature are configured to be inserted within the lumen of the medical implant, such that when the tubular distal portion and the second engagement fea-ture are inserted within the lumen of the medical implant, the second engagement feature fixedly attaches the second attachment part to the medical implant.

2. The system of claim 1, wherein the first engagement feature includes one or more protrusions extending radially outward from an outer surface of the tubular proximal portion of the first attachment part.

3. The system of claim 2, wherein the first engagement feature includes one or more recesses extending into the outer surface of the tubular proximal portion of the first attachment part.

4. The system of claim 3, wherein a portion of the wall of the elongate shaft is configured to extend into the one or more recesses such that when the tubular proximal portion and the first engagement feature are inserted within the lumen of the elongate shaft, the portion of the wall of the elongate shaft engages at least one of the one or more recesses and the one or more protrusions, thereby preventing withdrawal of the tubular proximal portion from the elon-gate shaft.

5. The system of claim 4, wherein the portion of the wall is at least one moveable tab.

6. The system of claim 5, wherein the at least one moveable tab is biased radially inward.

7. The system of claim 1, wherein the second engagement feature includes one or more protrusions extending radially outward from an outer surface of the tubular distal portion of the second attachment part.

8. The system of claim 7, wherein the second engagement feature includes one or more recesses extending into the outer surface of the tubular distal portion of the second attachment part.

9. The system of claim 8, wherein a portion of the wall of the medical implant is configured to extend into the one or more recesses such that when the tubular distal portion and the second engagement feature are inserted within the lumen of the medical implant, the portion of the wall of the medical implant engages at least one of the one or more recesses and the one or more protrusions, thereby preventing withdrawal of the tubular distal portion from the medical implant.

10. The system of claim 9, wherein the portion of the wall is at least one moveable tab that is biased radially inward.

11. The system of claim 1, wherein the first attachment part and/or the second attachment part is formed from a first metallic material, and the elongate shaft and/or the medical implant is formed from a second metallic material dissimilar from the first metallic material.

12. The system of claim 11, wherein the second metallic material is a shape memory alloy.

13. The system of claim 1, further including a release wire configured to extend through the lumen of the elongate shaft, a lumen through the first attachment part, and a lumen through the second attachment part.

* * * * *